(12) United States Patent
Nolan et al.

(10) Patent No.: US 11,883,310 B2
(45) Date of Patent: *Jan. 30, 2024

(54) REPOSITIONABLE AND REMOVABLE STENTS

(71) Applicant: BOSTON SCIENTIFIC SCIMED, INC., Maple Grove, MN (US)

(72) Inventors: Damien V. Nolan, Galway (IE); Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/866,936

(22) Filed: Jul. 18, 2022

(65) Prior Publication Data

US 2022/0346989 A1 Nov. 3, 2022

Related U.S. Application Data

(63) Continuation of application No. 16/572,891, filed on Sep. 17, 2019, now Pat. No. 11,399,970.

(Continued)

(51) Int. Cl.
*A61F 2/95* (2013.01)
*A61F 5/00* (2006.01)
(Continued)

(52) U.S. Cl.
CPC .............. *A61F 2/95* (2013.01); *A61F 5/0089* (2013.01); *A61F 2/90* (2013.01);
(Continued)

(58) Field of Classification Search
CPC ............ A61F 2/24–2424; A61F 2/2475; A61F 2/82–945; A61F 5/0003–0089; A61F 2250/0059
See application file for complete search history.

(56) References Cited

U.S. PATENT DOCUMENTS 5,238,004 A 8/1993 Sahatjian et al.
5,779,732 A 7/1998 Amundson
(Continued)

FOREIGN PATENT DOCUMENTS

EP 1518518 A2 3/2005
EP 1518518 A3 4/2005
(Continued)

OTHER PUBLICATIONS

International Search Report and Written Opinion dated Aug. 16, 2019 for International Application No. PCT/US2019/035239.
(Continued)

*Primary Examiner* — Rebecca S Preston
(74) *Attorney, Agent, or Firm* — Seager, Tufte & Wickhem, LLP

(57) ABSTRACT

An illustrative endoluminal implant having an elongated tubular member. The elongated tubular member having a stent and a retrieval suture interwoven with the stent. The retrieval suture including a first suture loop extending about a circumference of the stent and adjacent to a suture retrieval loop and a second suture loop extending about a circumference of the stent and longitudinally spaced from the first suture loop. The first and second suture loops coupled via one or more interconnecting segments. At least one of the first or second suture loops has an arc length of less than 270° of the circumference of the stent.

20 Claims, 14 Drawing Sheets

Related U.S. Application Data

(60) Provisional application No. 62/735,651, filed on Sep. 24, 2018.

(51) Int. Cl.
*A61F 2/90* (2013.01)
*A61F 2/04* (2013.01)
*A61F 2/848* (2013.01)

(52) U.S. Cl.
CPC . *A61F 2002/045* (2013.01); *A61F 2002/8483* (2013.01); *A61F 2002/9511* (2013.01); *A61F 2002/9528* (2013.01); *A61F 2002/9534* (2013.01); *A61F 2210/0014* (2013.01); *A61F 2220/0016* (2013.01); *A61F 2220/0075* (2013.01); *A61F 2250/001* (2013.01); *A61F 2250/0039* (2013.01); *A61F 2250/0059* (2013.01)

(56) References Cited

U.S. PATENT DOCUMENTS

| | | | |
|---|---|---|---|
| 5,984,957 A | 11/1999 | Laptewicz, Jr. et al. | |
| 6,508,803 B1 | 1/2003 | Horikawa et al. | |
| 6,669,724 B2 | 12/2003 | Park et al. | |
| 6,821,291 B2 | 11/2004 | Bolea et al. | |
| 6,974,471 B2 | 12/2005 | Van Schie et al. | |
| 7,018,401 B1 | 3/2006 | Hyodoh et al. | |
| 7,252,680 B2 | 8/2007 | Freitag | |
| 7,731,742 B2 | 6/2010 | Schlick et al. | |
| 7,833,280 B2 | 11/2010 | Stack et al. | |
| 8,372,134 B2 | 2/2013 | Schlick et al. | |
| 8,398,699 B2 | 3/2013 | Shin et al. | |
| 8,414,635 B2 | 4/2013 | Hyodoh et al. | |
| 8,876,880 B2 | 11/2014 | Hyodoh et al. | |
| 8,968,384 B2 | 3/2015 | Pearson et al. | |
| 9,050,168 B2 | 6/2015 | Neisz et al. | |
| 9,173,760 B2 | 11/2015 | Belhe et al. | |
| 9,271,854 B2 | 3/2016 | White et al. | |
| 9,301,862 B2 | 4/2016 | Jordan et al. | |
| 9,554,924 B2 | 1/2017 | Schlick et al. | |
| 9,801,749 B2 | 10/2017 | Hingston et al. | |
| 9,872,758 B2 | 1/2018 | Schlick et al. | |
| 11,399,970 B2 * | 8/2022 | Nolan | A61F 2/86 |
| 2002/0143387 A1 | 10/2002 | Soetikno et al. | |
| 2006/0276887 A1 | 12/2006 | Brady et al. | |
| 2007/0233230 A1 | 10/2007 | Nissl et al. | |
| 2008/0033528 A1 | 2/2008 | Satasiya et al. | |
| 2008/0109087 A1 | 5/2008 | Durgin | |
| 2010/0280591 A1 | 11/2010 | Shin et al. | |
| 2010/0280592 A1 | 11/2010 | Shin et al. | |
| 2011/0307070 A1 | 12/2011 | Clerc et al. | |
| 2012/0041538 A1 | 2/2012 | White et al. | |
| 2016/0081832 A1 | 3/2016 | Hingston et al. | |
| 2017/0056224 A1 | 3/2017 | Baxter et al. | |
| 2017/0189212 A1 | 7/2017 | Eller et al. | |
| 2017/0252195 A1 | 9/2017 | Stangenes et al. | |
| 2017/0290653 A1 | 10/2017 | Folan et al. | |
| 2017/0290983 A1 | 10/2017 | Sonderegger | |
| 2017/0325983 A1 | 11/2017 | Valdes et al. | |
| 2018/0125691 A1 | 5/2018 | Folan et al. | |
| 2021/0205065 A1 | 7/2021 | Cote et al. | |

FOREIGN PATENT DOCUMENTS

| | | |
|---|---|---|
| EP | 1870057 A1 | 12/2007 |
| EP | 2528554 B1 | 12/2012 |

OTHER PUBLICATIONS

International Search Report and Written Opinion dated Dec. 2, 2019 for International Application No. PCT/US2019/051406.

* cited by examiner

REPOSITIONABLE AND REMOVABLE STENTS

CROSS-REFERENCE TO RELATED APPLICATIONS

This application is a continuation of U.S. application Ser. No. 16/572,891, filed Sep. 17, 2019, which claims the benefit of priority under 35 U.S.C. § 119 of U.S. Provisional Application No. 62/735,651, filed Sep. 24, 2018, the entire disclosure of which is hereby incorporated by reference.

TECHNICAL FIELD

The present disclosure relates generally to methods and apparatuses for repositioning and/or removing stents or implants. More particularly, the disclosure relates to structures for collapsing repositionable and/or removable stents or implants.

BACKGROUND

Implantable stents are devices that are placed in a tubular body structure, such as a blood vessel, esophagus, trachea, biliary tract, colon, intestine, stomach or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery/retrieval devices as well as alternative methods for manufacturing and using medical devices and delivery/retrieval devices.

SUMMARY

This disclosure is directed to several alternative designs, materials, methods of manufacturing medical device structures and associated uses thereof, such as stents for preventing leaks after an anastomosis surgery and/or treating various gastro-intestinal, digestive, or other ailments.

In a first example, an implant may comprise an elongated tubular member. The elongated tubular member may comprise a stent having a proximal end region, a distal end region, and a circumference. A retrieval suture is interwoven with the stent. The retrieval suture may include a first suture loop extending circumferentially around the stent and adjacent to a suture retrieval loop and a second suture loop extending circumferentially around the stent and longitudinally spaced from the first suture loop. The first and second suture loops may be coupled via one or more interconnecting segments. At least one of the first or second suture loops may have an arc length of 270° or less of the circumference of the stent.

Alternatively or additionally to any of the examples above, in another example, the first and second suture loops may each have an arc length of 270° or less of the circumference of the stent.

Alternatively or additionally to any of the examples above, in another example, the at least one of the first or second suture loops may have an arc length of 180° or less of the circumference of the stent.

Alternatively or additionally to any of the examples above, in another example, the first and second suture loops may each have an arc length of 180° or less of the circumference of the stent.

Alternatively or additionally to any of the examples above, in another example, the first suture loop may be a discontinuous loop comprising two or more circumferential segments of the retrieval suture separated by the one or more interconnecting longitudinal segments.

Alternatively or additionally to any of the examples above, in another example, the retrieval suture may be a single unitary structure.

Alternatively or additionally to any of the examples above, in another example, the stent may include a first outer diameter adjacent the proximal end region and a second smaller outer diameter adjacent the distal end region.

Alternatively or additionally to any of the examples above, in another example, the first suture loop may be positioned adjacent to the proximal end region and the second suture loop may be positioned adjacent to the distal end region.

Alternatively or additionally to any of the examples above, in another example, a force exerted on the retrieval suture loop may be configured to partially collapse the stent adjacent to the second suture loop.

Alternatively or additionally to any of the examples above, in another example, once an outer diameter of the stent adjacent to the second suture loop is at least partially collapsed, the force exerted on the retrieval suture loop may be configured to collapse the stent adjacent to the first suture loop.

Alternatively or additionally to any of the examples above, in another example, the retrieval suture may further comprise a third suture loop extending circumferentially around the stent and longitudinally spaced from the second suture loop, the second and third suture loops coupled via one or more interconnecting segments.

Alternatively or additionally to any of the examples above, in another example, the elongated tubular member may further comprise a flexible sleeve extending distally from the distal end region of the stent.

Alternatively or additionally to any of the examples above, in another example, the retrieval suture may further comprise a third suture loop extending about a circumference of the flexible sleeve and longitudinally spaced from the second suture loop, the second and third suture loops coupled via one or more interconnecting segments.

Alternatively or additionally to any of the examples above, in another example, a force exerted on the retrieval suture loop may be configured to partially collapse the flexible sleeve adjacent to the third suture loop.

Alternatively or additionally to any of the examples above, in another example, once an outer diameter of the flexible sleeve adjacent to the third suture loop is at least partially collapsed, the force exerted on the retrieval suture loop may be configured to sequentially collapse the stent adjacent to the second suture loop followed by the stent adjacent to the first suture loop.

In another example, an implant may comprise an elongated tubular member. The elongated tubular member may comprise a stent having a proximal end and a distal end and a retrieval suture interwoven with the stent. The retrieval suture may comprise a first segment extending circumferentially between a first circumferential location and a second circumferential location, a second segment extending longitudinally between the second circumferential location and a third circumferential location, a third segment extending circumferentially between the third circumferential location and a fourth circumferential location, a fourth segment extending longitudinally between the fourth circumferential location and a fifth circumferential location, and a fifth segment extending circumferentially between the fifth circumferential location and a sixth circumferential location. The first, second, fifth, and sixth circumferential locations may be at a first longitudinal distance from the proximal end of the stent and the third and fourth circumferential locations may be at a second longitudinal distance, different from the first longitudinal distance, from the proximal end of the stent. The first and fifth segments may together form a discontinuous first suture loop and the third segment may form a second suture loop. At least one of the first or second suture loops may have an arc length of 270° or less of the circumference of the stent.

Alternatively or additionally to any of the examples above, in another example, the at least one of the first or second suture loops may have an arc length of 180° or less of the circumference of the stent.

Alternatively or additionally to any of the examples above, in another example, the retrieval suture may be a single unitary structure.

In another example, an implant may comprise an elongated tubular member. The elongate tubular member may comprise a stent having a proximal end region and a distal end region, the stent including a first outer diameter adjacent the proximal end region and a second smaller outer diameter adjacent the distal end region, a flexible sleeve extending distally from the distal end region of the stent, and a retrieval suture interwoven with the stent, the retrieval suture including a first suture loop extending about a circumference of the stent and adjacent to a suture retrieval loop, a second suture loop extending about a circumference of the stent and longitudinally spaced from the first suture loop, and a third suture loop extending about a circumference of the flexible sleeve and longitudinally spaced from the second suture loop, the first and second suture loops coupled via one or more interconnecting segments and the second and third suture loops coupled via one or more interconnecting segments. At least one of the first, second, or third suture loops may have an arc length of 270° or less of the circumference of the stent.

Alternatively or additionally to any of the examples above, in another example, the at least one of the first, second, or third suture loops may have an arc length of 180° or less of the circumference of the stent.

Alternatively or additionally to any of the examples above, in another example, the retrieval suture may be a single unitary structure.

Alternatively or additionally to any of the examples above, in another example, the first suture loop and the second suture loop may each be formed of discontinuous segments. The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
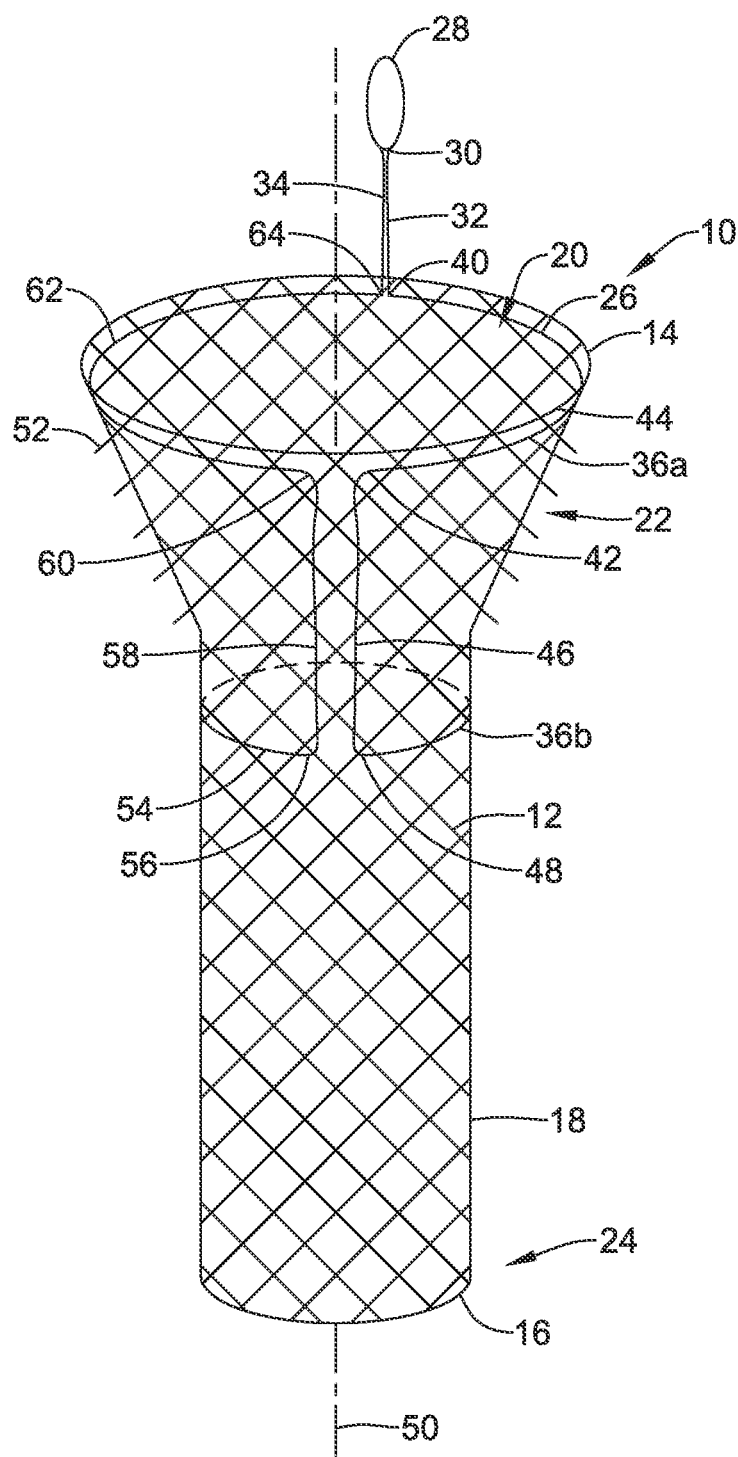
FIG. 1 is a side view of an illustrative implant with a retrieval suture in a first configuration.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Gastric outlet obstruction (GOO) is the clinical and pathophysiological consequence of any disease process that produces a mechanical impediment to gastric emptying. The presence of GOO can be classified into disease conditions that affect the antrum and pylorus that lead to pyloric dysfunction or disease conditions of the proximal duodenum that restrict efferent flow. Clinical conditions such as peptic ulcer disease (PUD), pyloric stenosis, and gastric polyps represent etiologies for the former with pancreatic carcinoma, ampullary cancer, duodenal cancer, cholangiocarcinomas representing etiologies for the latter. In some instances, GOO may be directly treated through stenting the location using gastrointestinal (GI) self-expanding stents. However, placing a stent across the pyloric valve may leave the pylorus in a continually open position. However, this may result in gastric leakage into the duodenum. Alternative stent designs are desired to allow the immediate blockage to be opened while allowing for natural pyloric function to be retained.

FIG. 1 illustrates a side view of an illustrative endoluminal implant or stent 10. In some instances, the stent 10 may be formed from an elongated tubular stent frame 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 20 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc.

The stent frame 12 may have a woven structure, fabricated from a number of filaments. In some embodiments, the stent frame 12 may be braided with one filament. In other embodiments, the stent frame 12 may be braided with several filaments, as is found, for example, in the WALL-FLEX®, WALLSTENT®, and POLYFLEX® stents, made and distributed by Boston Scientific Corp. In another embodiment, the stent frame 12 may be knitted, such as the ULTRAFLEX™ stents made by Boston Scientific Corp. In yet another embodiment, the stent frame 12 may be of a knotted type, such the PRECISION COLONIC™ stents made by Boston Scientific Corp. In still another embodiment, the stent frame 12 may be laser cut, such as the EPIC™ stents made by Boston Scientific Corp.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and ELGILOY®. Depending on the material selected for construction, the stent 10 may be self-expanding (i.e., configured to automatically radially expand when unconstrained). In some embodiments, fibers may be used to make the stent 10, which may be composite fibers, for example, having an outer shell made of Nitinol having a platinum core. It is further contemplated the stent 10 may be formed from polymers including, but not limited to, polyethylene terephthalate (PET). In some embodiments, the stent 10 may be self-expanding while in other embodiments, the stent 10 may be expand by an expansion device (such as, but not limited to a balloon inserted within the lumen 20 of the stent 10). As used herein the term "self-expanding" refers to the tendency of the stent to return to a preprogrammed diameter when unrestrained from an external biasing force (for example, but not limited to a delivery catheter or sheath). The stent 10 may include a one-way valve, such as an elastomeric slit valve or duck bill valve, positioned within the lumen 20 thereof to prevent retrograde flow of gastrointestinal fluids.

In some instances, in the radially expanded configuration, the stent 10 may include a first end region 22 proximate the proximal end 14 and a second end region 24 proximate the second end 16. In some embodiments, the first end region 22 and the second end region 24 may include retention features or anti-migration flared regions (not explicitly shown at the second end region 24) having enlarged diameters relative to the intermediate portion 18. The anti-migration flared regions, which may be positioned adjacent to the first end 14 and the second end 16 of the stent 10, may be configured to engage an interior portion of the walls of the esophagus, stomach or other body lumen. In some embodiments, the retention features, or flared regions may have a larger diameter than the cylindrical intermediate region 18 of the stent 10 to prevent the stent 10 from migrating once placed in the esophagus, stomach, or other body lumen. It is contemplated that a transition from the cross-sectional area of the intermediate region 18 to the retention features or flared regions may be gradual, sloped, or occur in an abrupt step-wise manner, as desired. In other embodiments, the stent 10 may have a uniform diameter from the proximal end 14 to the distal end 16.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and ELGILOY®. Depending on the material selected for construction, the stent 10 may be self-expanding or require an external force to expand the stent 10. In some embodiments, composite filaments may be used to make the stent 10, which may include, for example, an outer shell or cladding made of Nitinol and a core formed of platinum or other radiopaque material. It is further contemplated the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

The implant 10 may be may be entirely, substantially or partially, covered with a polymeric covering, such as a coating (not explicitly shown). The covering may be disposed on an inner surface and/or outer surface of the implant 10, as desired. When so provided a polymeric covering may reduce or eliminate tissue ingrowth and/or reduce food impaction.

The implant 10 may further include a retrieval suture 26. The suture 26 may include a retrieval suture loop 28 which may be configured to be grasped by forceps or other tool during a clinical procedure for stent removal and or repositioning. In some cases, the retrieval suture loop 28 may be formed by tying a knot 30 between, or otherwise coupling (e.g., heat bonding, adhesive, etc.) a first end 32 and a second end 34 of the retrieval suture. In other embodiments, the retrieval suture loop 28 may be formed at either the first end 32 or the second end 34 of the retrieval suture 26. In such an instance, the end 32, 34 free from the retrieval suture loop 28 may be coupled to the stent 10 or the opposing end 32, 34 of the retrieval suture 26, although this is not required.

The suture 26 may be interwoven with the stent frame 12 at intervals along a length of the implant 10 to create a plurality of suture loops 36a, 36b (collectively, 36). While the illustrative implant 10 is shown and described has having two suture loops 36, it is contemplated that the implant 10 may include more than two suture loops 36, as desired. For example, the implant 10 may include three, four, five, or more suture loops 36. It is contemplated that the suture loops 36 may be positioned at regular or even intervals throughout the overall length of the implant 10. However, in other embodiments, the suture loops 36 may be positioned at eccentric or uneven intervals along the length of the implant 10, as desired. It is contemplated that the suture loops 36 may be positioned to facilitate retrieval, repositioning, and/or reshaping of the stent 10. For example, in a stent 10 having two or more flared or enlarged regions, as in the AXIOS® stent made and distributed by Boston Scientific Corp., a first retrieval suture loop 36a may be positioned adjacent to the first flare and a second retrieval suture loop 36b may be positioned adjacent to the second flare.

In some embodiments, one, two or more, or all of the suture loops 36 may extend entirely around the circumference (e.g., 360°) of the stent frame 12. In other embodiments, one, two or more, or all of the suture loops 36 may extend or have an arc length of less than 360° about the circumference of the stent frame 12. In some embodiments, one or more of the suture loops 36 may extend or have an arc length of 350° or less, 300° or less, 270° or less, 225° or less, 180° or less, 135° or less, etc. In yet other embodiments, one, two or more, or all of the suture loops may extend more than 360° about the circumference of the stent frame 12.

The suture loops 36 may be formed from a single unitary suture 26. It is contemplated that the suture 26 may be interwoven with the stent frame 12 such that the suture loops 36 may be constrained in a predetermined sequential order. In some cases, the proximal loop 36a may not extend in a continuous loop. Rather, the proximal loop 36a may be broken into sections by longitudinally extending interconnecting segments 46, 58 which extend between the proximal loop 36a and the distal loop 36b.

The suture 26 may be interwoven with the stent frame 12 by threading one of the ends 32, 34 around the proximal end 14 of the implant 10 beginning at a first circumferential location 40 and moving (e.g., threading) in a first direction. In the illustrative example, the suture 26 is described as initially being threaded in a clockwise direction. However, the reverse configuration in which the suture is initially threaded in a counterclockwise direction is also contemplated. The suture 26 may be threaded around about one half of the circumference of the implant 10 such that a first segment 44 of the suture 26 extends between the first circumferential location 40 and a second circumferential location 42. The first and second circumferential locations 40, 42 may be positioned at a similar longitudinal distance (e.g., in a direction extending generally parallel to the longitudinal axis 50 of the implant 10) from the first end 14 of the implant 10. In some cases, the suture 26 may be threaded such that it is interwoven with the stent frame 12 such that a portion of the suture 26 is within the lumen 20 of the implant 10 and a portion of the suture 26 is positioned along an exterior surface of the implant 10 (e.g., such that it will be in contact with a vessel lumen when the implant 10 is deployed within the body). At the second circumferential location 42, the suture 26 may be threaded along a length of implant 10 in a direction towards the second end 16 such that a second longitudinally extending interconnecting segment 46 of the suture 26 extends along a length of the implant 10 in a generally linear direction. The length of the second segment 46 of the suture 26 may vary depending on the application. For example, some implants 10 may include radially extending quills 52 configured to engage a body tissue. The second segment 46 may be configured to extend along a length equal to or greater to a length of the implant 10 including the radially extending quills 52. This is just one example. Other features of the implant 10, such as, but not limited to, the length of the implant 10 may be used to determine the length of the second segment 46 of the suture 26.

The second segment 46 of the suture 26 may extend from the second circumferential location 42 to a third circumferential location 48. The second circumferential location and the third circumferential location 48 may be at similar radial points about the circumference of the implant 10 but spaced a distance along the length thereof. At the third circumferential location 48, a third segment 54 of the suture 26 may be threaded radially about the circumference of the implant 10 in a second direction (e.g., counterclockwise), opposite to the first direction. The third segment 54 may extend between the third circumferential location 48 and a fourth circumferential location 56 to form a suture loop 36b. In some embodiments, the third circumferential location 48 and the fourth circumferential location 56 may be at substantially the same radial point about the circumference of the implant 10 such that the suture loop 36b extends substantially or entirely 360° about the circumference of the implant 10. In other embodiments the third circumferential location 48 and the fourth circumferential location 56 may be radially spaced from one another by, for example, 1° or less, 5° or less, 10° or less, 20° or less, etc.

At the fourth circumferential location 56, the suture 26 may be threaded along a length of implant 10 in a direction towards the first end 14 such that a fourth longitudinally extending interconnecting segment 58 of the suture 26 extends along a length of the implant 10 in a direction to the longitudinal axis 50. The length of the fourth segment 58 of the suture 26 may be about the same length as the second segment 46 of the suture 26. The fourth segment 58 of the suture 26 may extend between the fourth circumferential location 56 and a fifth circumferential location 60. In some cases, the second and/or fourth segments 46, 58 of the suture may not be interwoven with the stent body 12 but rather extend along an inner or outer surface of the stent body 12. In some embodiments, the first, second, and fifth circumferential locations 40, 42, 60 may be positioned at a similar longitudinal distance (e.g., in a direction extending generally parallel to the longitudinal axis 50 of the implant 10) from the first end 14 of the implant 10.

From the fifth circumferential location 60, the suture 26 may be threaded through the stent body 12 in the first direction (e.g., away from the first segment 44) to form fifth segment 62 of the suture 26. The fifth segment 62 of the suture 26 may be threaded through the stent body 12 to a sixth circumferential location 64 and/or until it meets the first circumferential location 40 (e.g., the starting point) to form the proximal loop 36a. As described above, the proximal suture loop 36a may be formed of discontinuous or broken segments 44, 62. In some embodiments, the fifth segment 62 ceases to be interwoven with the stent body 12 before the suture 26 reaches the first circumferential location 40. For example, the first circumferential location 40 may be radially spaced from the sixth circumferential location 64 by, for example, 1° or less, 5° or less, 10° or less, 20° or less, etc. A first end 32 of the suture 26 may extend from the first circumferential location 40 and the second end 34 of the suture 26 may extend from the sixth circumferential location 64. The ends 32, 34 of the suture 26 may be tied to form a knot 30, glued, and the knot 30 subsequently cured.

It is contemplated that in embodiments where it is desired for the suture 26 to include suture loops 36 which extend around less than the entire circumference, the suture 26 may be initially threaded about half of the length of the desired final arc. For example, as will be described in more detail herein, if the finished suture loop 36 is to extend about 180° about the circumference of the implant 10, the suture 26 may be initially threaded about 90° around the circumference before being threaded down a length of the implant 10.

Figure 2:
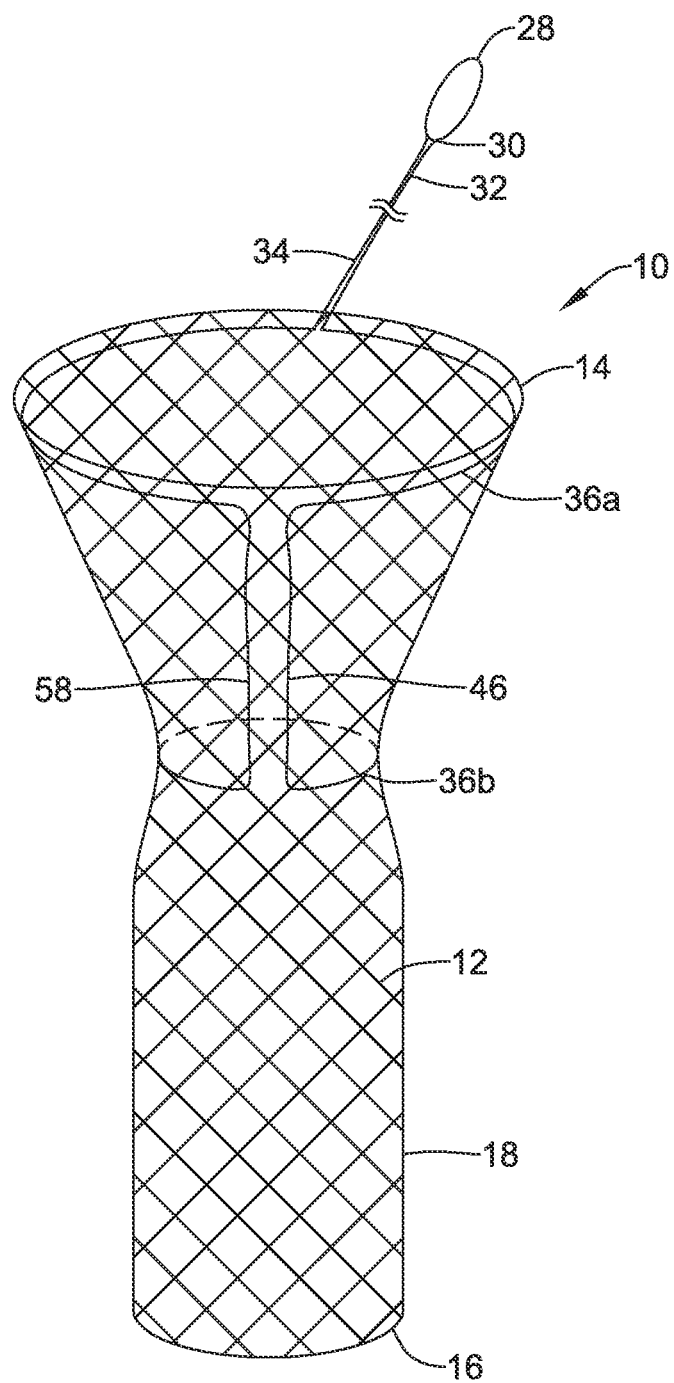
FIG. 2 is a side view of the illustrative implant of FIG. 1 in a first collapsed configuration.
Figure 3:
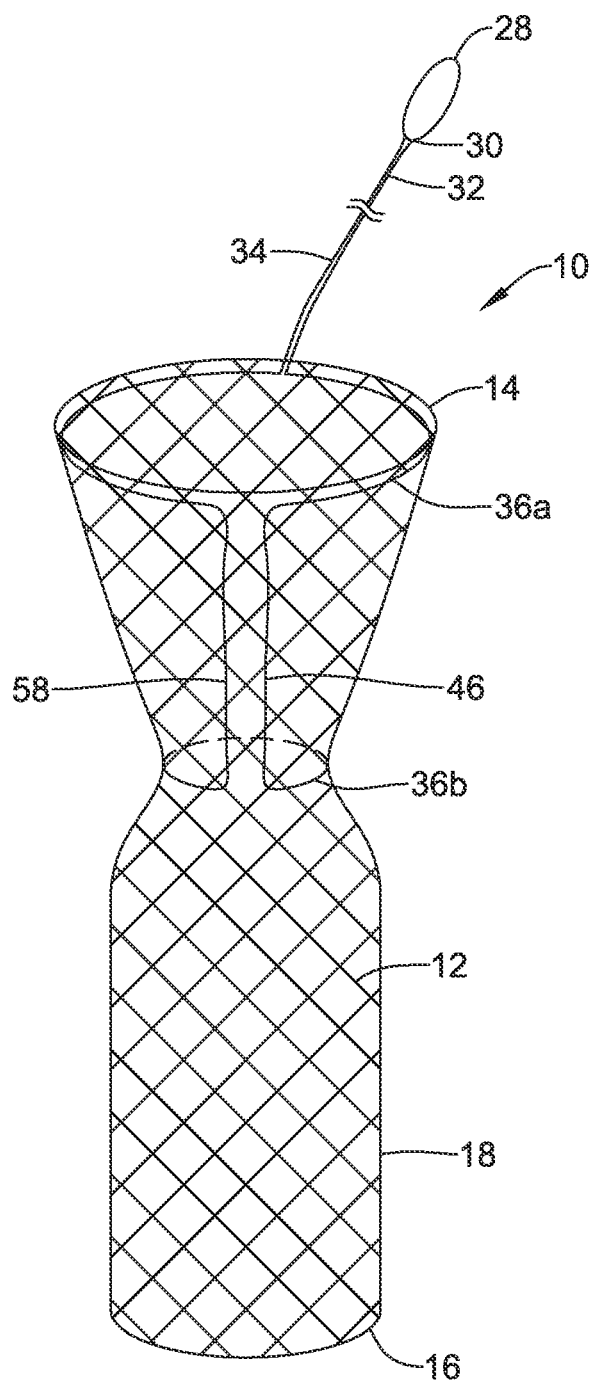
FIG. 3 is a side view of the illustrative implant of FIG. 1 in a second collapsed configuration.

To collapse the implant 10, the retrieval suture loop 28, or the first suture loop 36a in the absence of the retrieval suture loop 28, may be pulled or otherwise actuated in a proximal direction. It is contemplated that the direction of actuation (e.g., proximal or distal) required to actuate the suture 26 may be dependent on the direction in which the suture 26 is interwoven with the stent frame 12. As the retrieval suture loop 28, or the first suture loop 36a in the absence of the retrieval suture loop 28, is actuated, the suture loops 36 begin to constrain or reduce the diameter of the implant 10, as shown in FIG. 2, which illustrates a side view of the illustrative implant 10 during suture 26 actuation. The distal or second suture loop 36b may be constrained first, causing the intermediate portion 18 of the stent body 12 to collapse or reduce in diameter before the first end 14. Continued actuation of the retrieval suture loop 28 may cause first end 14 of the implant 10 to also be reduced in diameter, as shown in FIG. 3. It is contemplated that the proximal or first suture loop 36a may not be actuated until the slack is removed from the preceding longitudinally extending suture loop 36b and the suture connection links 46, 58 are drawn taut to apply a force to the next suture loop 36a. However, this is not required. In some instances, the connection links 46, 58 may have a length such that the suture loops 36 simultaneously (or approximately simultaneously) constrain the implant 10 along its length.

Figure 4:
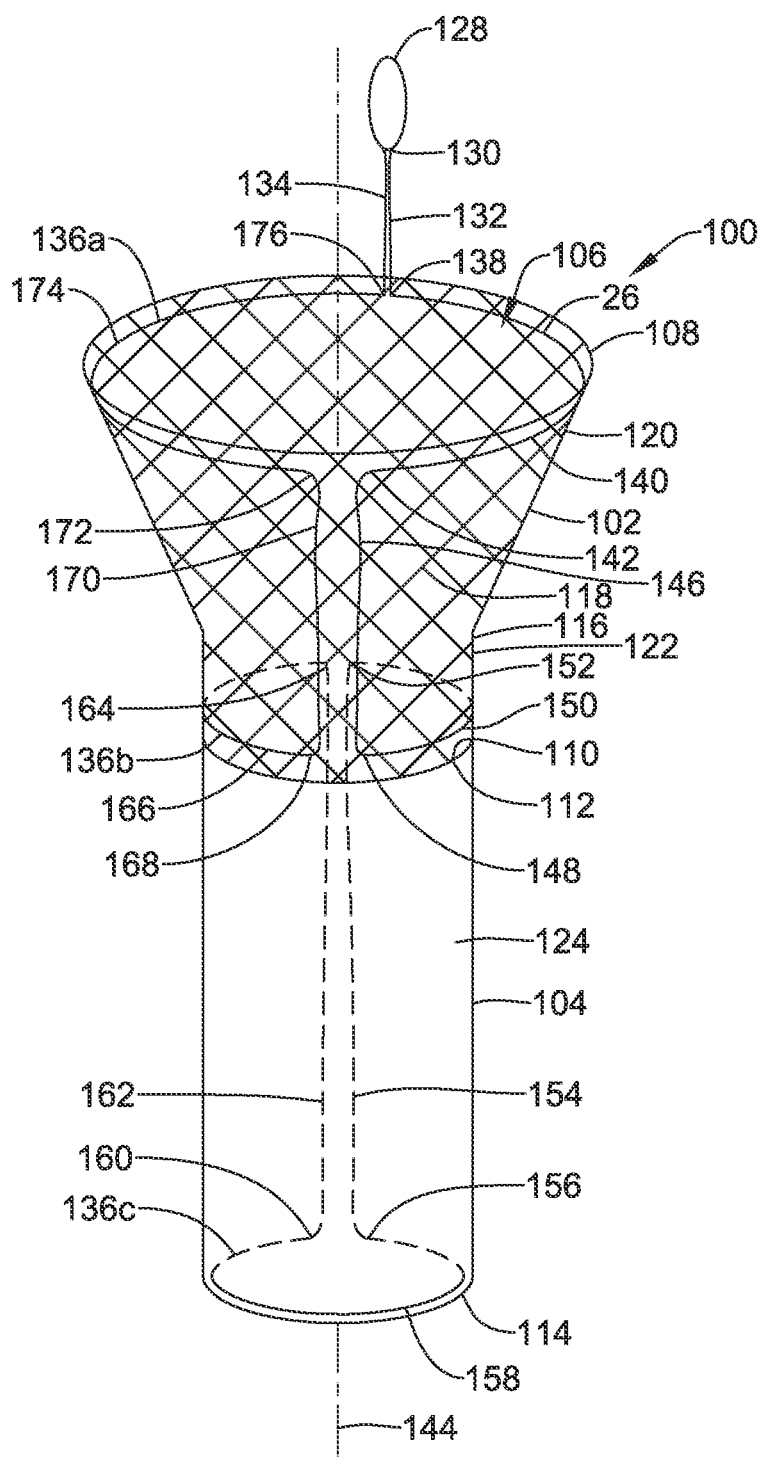
FIG. 4 is a side view of another illustrative implant with a retrieval suture in a first configuration.

FIG. 4 illustrates a side view of another illustrative endoluminal implant 100 including a plurality of regions, including, a first or proximal region 102 and a second or distal region 104. While the illustrative implant 100 is shown and described as having two regions 102, 104, it is contemplated the implant 100 may include any number of regions desired, such as, but not limited to, one, two, three, four, or more. Further, the regions 102, 104 may be any combination of structures and materials desired. In some cases, the implant 100 may include features (e.g., anti-migration flares, fixation spikes, sutures, etc.) to prevent distal/proximal displacement and/or migration of the implant 100, once the implant 100 is positioned and expanded in the body lumen. The implant 100 may include a lumen 106 extending entirely through the length of the implant 10, such as from a proximal end 108 of the first region 102 to a distal end 114 of the second region 104.

In some cases, the first region 102 may take the form of a stent 116 including an elongated tubular stent frame 118 defining a lumen. The stent 116 may be may be entirely, substantially, or partially covered with a polymeric covering, such as a coating (not explicitly shown). The covering may be disposed on an inner surface and/or outer surface of the stent 116, as desired. When so provided a polymeric covering may reduce or eliminate tissue ingrowth and/or reduce food impaction through interstices of the stent 116 into the lumen. It is contemplated that leaving an outer rim or a portion of the surface uncovered, an area of hyperplasia can be generated which would create a seal. The stent 116 may include regions of differing diameters. For example, the stent 116 may include a flared (e.g., enlarged relative to other portions of the stent 116) proximal end region 120 tapering radially inward to a constant diameter distal end region 122. While not explicitly shown, the stent 116 may include regions increasing diameters (e.g., in the distal direction), if so desired. The stent frame 118 may be expandable between a radially collapsed delivery configuration and a radially expanded deployed configuration. The expanded configuration may secure the implant 100 at the desired location in a body lumen.

The stent frame 118 may have a woven structure, fabricated from a number of filaments. In some embodiments, the stent frame 118 may be knitted with one filament, as is found, for example, in the ULTRAFLEX™ stents, made and distributed by Boston Scientific Corp. In other embodiments, the stent frame 118 may be braided with several filaments, as is found, for example, in the WALLFLEX®, WALLSTENT®, and POLYFLEX® stents, made and distributed by Boston Scientific Corp. In yet another embodiment, the stent frame 118 may be of a knotted type, such the PRECISION COLONIC™ stents made by Boston Scientific Corp. In still another embodiment, the stent frame 118 may be laser cut, such as the EPIC™ stents made by Boston Scientific Corp. It is contemplated that the stent frame 118 may be formed having the same structure as one another or having a different structure from one another.

It is contemplated that the stent frame 118 can be made from a number of different materials such as, but not limited to, metals, metal alloys, shape memory alloys, and/or polymers, as desired, enabling the stent 116 to be expanded into shape when accurately positioned within the body. The material of the stent frame 118 may be the same or different, as desired. In some instances, the material may be selected to enable the stent 116 to be removed with relative ease as well. For example, the stent frame 118 can be formed from alloys such as, but not limited to, nitinol and ELGILOY®. Depending the on material selected for construction, the stent 116 may be self-expanding (i.e., configured to automatically radially expand when unconstrained). In some embodiments, fibers may be used to make the stent frame 118, which may be composite fibers, for example, having an outer shell made of nitinol having a platinum core. It is further contemplated the stent frame 118 may be formed from polymers including, but not limited to, polyethylene terephthalate (PET). In some embodiments, the stent 116 may be self-expanding while in other embodiments, the stent 116 may be expanded by an expansion device (such as, but not limited to a balloon inserted within a lumen 106 of the implant 100). As used herein the term "self-expanding" refers to the tendency of the stent to return to a preprogrammed diameter when unrestrained from an external biasing force (for example, but not limited to a delivery catheter or sheath).

The stent 116 may include a one-way valve, such as an elastomeric slit valve or duck bill valve, positioned within the lumen 106 thereof to prevent retrograde flow of fluid or other material, such as gastrointestinal fluids.

In some cases, the second region 104 may take the form of a flexible sleeve 124. The flexible sleeve 124 may extend between a proximal end 112 adjacent to the distal end 110 of the stent 116 and a distal end 114 extending distally therefrom. For example, the sleeve 124 may be connected, affixed, or secured to the distal end region 122 of the first or stent 116 adjacent to a proximal end region 112 of the sleeve 124. In some cases, the sleeve 124 may overlap a portion or all of the stent 116. In some instances, the sleeve 124 may be devoid of any structural components tending to hold the lumen 106 through the sleeve 124 open, thus allowing the sleeve 124 to collapse inward upon itself when subjected to an external force (such as, but not limited to a pyloric valve) thus closing off the lumen 106. In some embodiments, the sleeve 124 may extend partially, substantially, or all of the length of the implant 100 and cover all other portions (exterior surface and/or interior surface) of the implant 100, including the stent 116. Said differently, while the regions 102, 104 have been described as a stent 116 or a sleeve 124, each region may include one or both of a frame structure and flexible sleeve structure. The sleeve 124 may be secured to the stent 116 by an adhesive or other methods known in the art, including by not limited to thermal methods, mechanical methods, etc.

The sleeve 124 may have an elongated, tubular shape defining a lumen. The lumen of the stent 116 and the flexible sleeve 124 may be fluidly connected to form the lumen 106 of the implant 100. It is contemplated that one or more of the regions 102, 104 of the implant 100 may include more than one lumen, as desired. The sleeve 124 may be a thin flexible membrane that readily collapses on itself. For example, the sleeve 124 may be configured to collapse upon itself under the applied radial force exerted by a natural valve or sphincter when the implant 100 is deployed in a body lumen having a natural valve or sphincter. However, the sleeve 124 may be provided with a radial support to hold it in the expanded configuration. Some examples and discussion of illustrative supports may be found in Patent Application No. 62/419,707, filed on Nov. 9, 11616, titled DEPLOYABLE SLEEVES AND RELATED METHODS, the disclosure of which is incorporated herein by reference.

The sleeve 124 may include one or more of the following polymer materials: polyethylene, polypropylene, polystyrene, polyester, biosorbable plastics (e.g., polylactic acid), polycarbonate, polyvinyl chloride, polyacrylate, acrylate, polysulfone, polyetheretherketone, thermoplastic elastomers, thermoset elastomers (e.g., silicone), poly-p-xylylene (parylene), flouropolymers (e.g., polytetrafluoroethylene (PTFE), polyvinylidene fluoride (PVDF), poly(vinylidene fluoride-co-hexafluoropropylene) (PVDFHFP)), bioplastics (e.g., cellulose acetate). The sleeve 124 may additionally or alternatively include one or more of: polyurethane and its copolymers, ethylene vinyl-acetate, polyethylene terephthalate (PET), polyolefins, cellulosics, polyamides, acrylonitrile butadiene styrene copolymers, styrene isoprene butadiene (SIBS) block copolymers, acrylics, poly(glycolide-lactide) copolymer, Tecothane, PEBAX, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed, such as, but not limited to Chrono-Flex®, manufactured by AdvanSource Biomaterials, based in Wilmington, MA, a family of biodurable aromatic polycarbonate based thermoplastic urethanes.

In further detail, the implant 100 may be generally cylindrical in shape, although this is not required, substantially flexible, and sized appropriately for a convenient accommodation within the digestive tract. It is contemplated that various shapes, sizes and designs of the implant may be constructed depending on the size and geometry of the cavities where the implant 100 has to be placed. In various examples, the implant 100 may have a length between 3-102 inches, 3-6 inches, 0.5-116 feet (0.15-6.1 meters), between 3-5 feet (0.9-1.5 meters), or about 2-4 feet (0.6-1.2 meters). However, the implant 100 may have a length of less than 0.5 feet (0.15 meters) or greater than 116 feet (6.1 meters) in some instances.

Once implanted in a patient, the stent 116 may exert a radially outward force to help secure the implant 100 to the body lumen. The implant 100 may be positioned in the antrum-pyloric-duodenum, esophagus, the gastro-esophageal junction (GEJ) region (e.g., at or near the cardia with the sleeve extending into the esophagus), or at or near the pylorus with the sleeve extending through the stomach or other portions of the gastro-intestinal system. In one example, the implant 100 may be positioned such that the stent 116 is positioned at the stomach outlet with the sleeve 124 bridging the pylorus. The flared structure of the stent 116 may use the stomach to anchor the implant 100 and act as an anti-migration mechanism for the implant 10. For example, the large outer diameter of the proximal end 108 of the stent 116 may engage the stomach outlet to prevent or limit movement of the implant 100.

The implant 100 may further include a retrieval suture 126. The suture 126 may include a retrieval suture loop 128 which may be configured to be grasped by forceps or other tool during a clinical procedure for stent removal and or repositioning. In some cases, the retrieval suture loop 128 may be formed by tying a knot 130 between, or otherwise coupling (e.g., heat bonding, adhesive, etc.) a first end 132 and a second end 134 of the retrieval suture. In other embodiments, the retrieval suture loop 128 may be formed at either the first end 132 or the second end 134 of the retrieval suture 126. In such an instance, the end 132, 134 free from the retrieval suture loop 128 may be coupled to the stent 100 or the opposing end 132, 134 of the retrieval suture 126, although this is not required.

The suture 126 may be interwoven with the stent frame 118 at intervals along a length of the implant 100 to create a plurality of suture loops 136a, 136b, 136c (collectively, 136). While the illustrative implant 100 is shown and described has having three suture loops 136, it is contemplated that the implant 100 may include fewer than or more than three suture loops 136, as desired. For example, the implant 100 may include two, three, four, five, or more suture loops 136. It is contemplated that the suture loops 136 may be positioned at regular or even intervals throughout the overall length of the implant 100. However, in other embodiments, the suture loops 136 may be positioned at eccentric or uneven intervals along the length of the implant 100, as desired. In some embodiments, one, two or more, or all of the suture loops 136 may extend entirely around the circumference (e.g., 360°) of the stent frame 118. In other embodiments, one, two or more, or all of the suture loops 136 may extend less than 360° about the circumference of the stent frame 118. In some embodiments, one or more of the suture loops 136 may extend 350° or less, 300° or less, 270° or less, 225° or less, 180° or less, 135° or less, etc. In yet other embodiments, one, two or more, or all of the suture loops may extend more than 360° about the circumference of the stent frame 118.

The suture loops 136 may be formed from a single unitary suture 126. It is contemplated that the suture 126 may be interwoven with the stent frame 118 such that the suture loops 136 may be constrained in a predetermined sequential order. In some cases, the proximal loop 136a and/or the intermediate loop 136b may not extend in a continuous loop. Rather, the proximal loop 136a and/or the intermediate loop 136b may be broken into sections by longitudinally extending interconnecting links or segments 146, 170 which extend between the proximal loop 136a and the intermediate loop 136b and by longitudinally extending interconnecting links or segments 154, 162 which extend between the intermediate loop 136b and the distal loop 136b.

The suture 126 may be interwoven with the stent frame 118 by threading one of the ends 132, 134 around the proximal end 108 of the implant 100 beginning at a first circumferential location 138 and moving (e.g., threading) in a first direction. In the illustrative example, the suture 126 is described as initially being threaded in a clockwise direction. However, the reverse configuration in which the suture is initially threaded in a counterclockwise direction is also contemplated. The suture 126 may be threaded around about one half of the circumference of the implant 100 such that a first segment 140 of the suture 126 extends between the first circumferential location 138 and a second circumferential location 142. The first and second circumferential locations 138, 142 may be positioned at a similar longitudinal distance (e.g., in a direction extending generally parallel to the longitudinal axis 144 of the implant 100) from the first end 108 of the implant 100. In some cases, the suture 126 may be threaded such that it is interwoven with the stent frame 118 such that a portion of the suture 126 is within the lumen 106 of the implant 100 and a portion of the suture 126 is positioned along an exterior surface of the implant 100 (e.g., such that it will be in contact with a vessel lumen when the implant 100 is deployed within the body).

At the second circumferential location 142, the suture 126 may be threaded along a length of implant 100 in a direction towards the distal end 110 such that a second longitudinally extending interconnecting segment 146 of the suture 126 extends along a length of the implant 100 in a generally linear direction. The length of the second segment 146 of the suture 126 may vary depending on the application. For example, some implants 100 may include radially extending quills (not explicitly shown) configured to engage a body tissue. The second segment 146 may be configured to extend along a length equal to or greater to a length of the implant 100 including the radially extending quills. This is just one example. Other features of the implant 100, such as, but not limited to, the length of the implant 100 and/or the length of the stent 116 portion may be used to determine the length of the second segment 146 of the suture 126.

The second segment 146 of the suture 126 may extend from the second circumferential location 142 to a third circumferential location 148. The second circumferential location 142 and the third circumferential location 148 may be at similar radial points about the circumference of the implant 100 but spaced a distance along the length thereof. At the third circumferential location 148, a third segment 150 of the suture 126 may be threaded in a radial direction about the circumference of the implant 100 in a second direction (e.g., counterclockwise), opposite to the first direction. The suture 126 may be threaded around about one half of the circumference of the implant 100 such that the third segment 150 of the suture 126 extends between the third circumferential location 148 and a fourth circumferential location 152 to form a segment of the intermediate suture loop 136b. In some embodiments, the third circumferential location 148 and the fourth circumferential location 152 may be may be positioned at a similar longitudinal distance (e.g., in a direction extending generally parallel to the longitudinal axis 144 of the implant 100) from the first end 108 of the implant 100.

At the fourth circumferential location 152, the suture 126 may be threaded along a length of implant 100 in a direction towards the distal end 114 of the sleeve 124 such that a fourth longitudinally extending interconnecting segment 154 of the suture 126 extends along a length of the implant 100 in a generally linear direction. The length of the fourth segment 154 of the suture 126 may vary depending on the application. In some cases, the fourth segment 154 may extend to the distal end 114 of the sleeve 124, although this is not required. In other embodiments, the fourth segment 154 may extend to a point proximal to the distal end 114 of the sleeve 124. The fourth segment 152 of the suture 126 may extend between the fourth circumferential location 152 and a fifth circumferential location 156. The fourth circumferential location 152 and the fifth circumferential location 156 may be at similar radial points about the circumference of the implant 100 but spaced a distance along the length thereof.

At the fifth circumferential location 156, a fifth segment 158 of the suture 126 may be threaded in a radial direction about the circumference of the implant 10 in the first direction (e.g., the same direction as the first segment 140). The fifth segment 158 may extend between the fifth circumferential location 156 and a sixth circumferential location 160 to form the distal suture loop 136c. In some embodiments, the fifth circumferential location 156 and the sixth circumferential location 160 may be at substantially the same radial point about the circumference of the implant 100 such that the distal suture loop 136c extends substantially or entirely 360° about the circumference of the implant 100. In other embodiments the fifth circumferential location 156 and the sixth circumferential location 160 may be radially spaced from one another by, for example, 1° or less, 5° or less, 10° or less, 20° or less, etc.

At the sixth circumferential location 160, the suture 126 may be threaded along a length of implant 100 in a direction towards the first end 108 such that a sixth longitudinally extending interconnecting segment 162 of the suture 126 extends along a length of the implant 100 in a linear direction generally parallel to the longitudinal axis 144. The length of the sixth segment 162 of the suture 126 may be about the same length as the fourth segment 154 of the suture 126. The sixth segment 162 of the suture 126 may extend between the sixth circumferential location 160 and a seventh circumferential location 164. In some cases, the fourth and/or sixth segments 154, 162 of the suture 126 may not be interwoven with the stent body 118 and/or flexible sleeve 124 but rather extend along an inner or outer surface of the stent body 118 and/or flexible sleeve 124.

At the seventh circumferential location 164, a seventh segment 166 of the suture 126 may be threaded in a radial direction about the circumference of the implant 100 in the second direction (e.g., counterclockwise), opposite to the first direction. The suture 126 may be threaded around about one half of the circumference of the implant 100 such that the seventh segment 166 of the suture 126 extends between the seventh circumferential location 164 and an eighth circumferential location 168 to form another portion of the intermediate suture loop 136*b*. Together, the third segment 150 and the seventh segment 166 of the suture 126 may form the intermediate suture loop 136*b*. In some embodiments, the seventh circumferential location 164 and the eighth circumferential location 168 may be positioned at a similar longitudinal distance (e.g., in a direction extending generally parallel to the longitudinal axis 144 of the implant 100) from the first end 108 of the implant 100. It is further contemplated that the seventh and eighth circumferential locations 164, 168 may be positioned at a similar longitudinal distance from the first end 108 of the implant 100 as the third and fourth circumferential locations 148, 152. In some embodiments, the seventh circumferential location 164 and the eighth circumferential location 168 may be at substantially the same radial point about the circumference of the implant 100 such that the intermediate suture loop 136*b* extends substantially or entirely 360° about the circumference of the implant 100. In other embodiments the seventh circumferential location 164 and the eighth circumferential location 168 may be radially spaced from one another by, for example, 1° or less, 5° or less, 10° or less, 20° or less, etc.

At the eighth circumferential location 168, the suture 126 may be threaded along a length of implant 100 in a direction towards the first end 108 such that an eighth longitudinally extending interconnecting segment 170 of the suture 126 extends along a length of the implant 100 in a linear direction generally parallel to the longitudinal axis 144. The length of the eighth segment 170 of the suture 126 may be about the same length as the second segment 146 of the suture 126. The eighth segment 170 of the suture 126 may extend between the eighth circumferential location 168 and a ninth circumferential location 172. In some cases, the second and/or eighth segments 146, 170 of the suture 126 may not be interwoven with the stent body 118 and/or flexible sleeve 124 but rather extend along an inner or outer surface of the stent body 118 and/or flexible sleeve 124.

At the ninth circumferential location 172, a ninth segment 174 of the suture 126 may be threaded in a radial direction about the circumference of the implant 100 in the first direction (e.g., clockwise). The suture 126 may be threaded around about one half of the circumference of the implant 100 such that the ninth segment 172 of the suture 126 extends between the ninth circumferential location 172 and a tenth circumferential location 176 to form another portion of the proximal suture loop 136*a*. Together, the first segment 140 and the ninth segment 174 of the suture 126 may form the proximal suture loop 136*a*. In some embodiments, the ninth circumferential location 172 and the tenth circumferential location 176 may be positioned at a similar longitudinal distance (e.g., in a direction extending generally parallel to the longitudinal axis 144 of the implant 100) from the first end 108 of the implant 100. It is further contemplated that the ninth and tenth circumferential locations 172, 176 may be positioned at a similar longitudinal distance from the first end 108 of the implant 100 as the first and second circumferential locations 138, 142. In some embodiments, the ninth circumferential location 172 and the tenth circumferential location 176 may be at substantially the same radial point about the circumference of the implant 100 such that the proximal suture loop 136*a* extends substantially or entirely 360° about the circumference of the implant 100. In other embodiments the ninth circumferential location 172 and the tenth circumferential location 176 may be radially spaced from one another by, for example, 1° or less, 5° or less, 10° or less, 20° or less, etc. A first end 132 of the suture 126 may extend from the first circumferential location 138 and the second end 134 of the suture 126 may extend from the tenth circumferential location 176. The ends 132, 134 of the suture 126 may be tied to form a knot 130, glued, and the knot 130 subsequently cured.

It is contemplated that in embodiments where it is desired for the suture 126 to include suture loops 136 which extend around less than the entire circumference, the suture 126 may be initially threaded about half of the length of the desired final arc. For example, as will be described in more detail herein, if the finished suture loop 136 is to extend about 180° about the circumference of the implant 100, the suture 126 may be initially threaded about 90° around the circumference before being threaded down a length of the implant 100.

Figure 5:
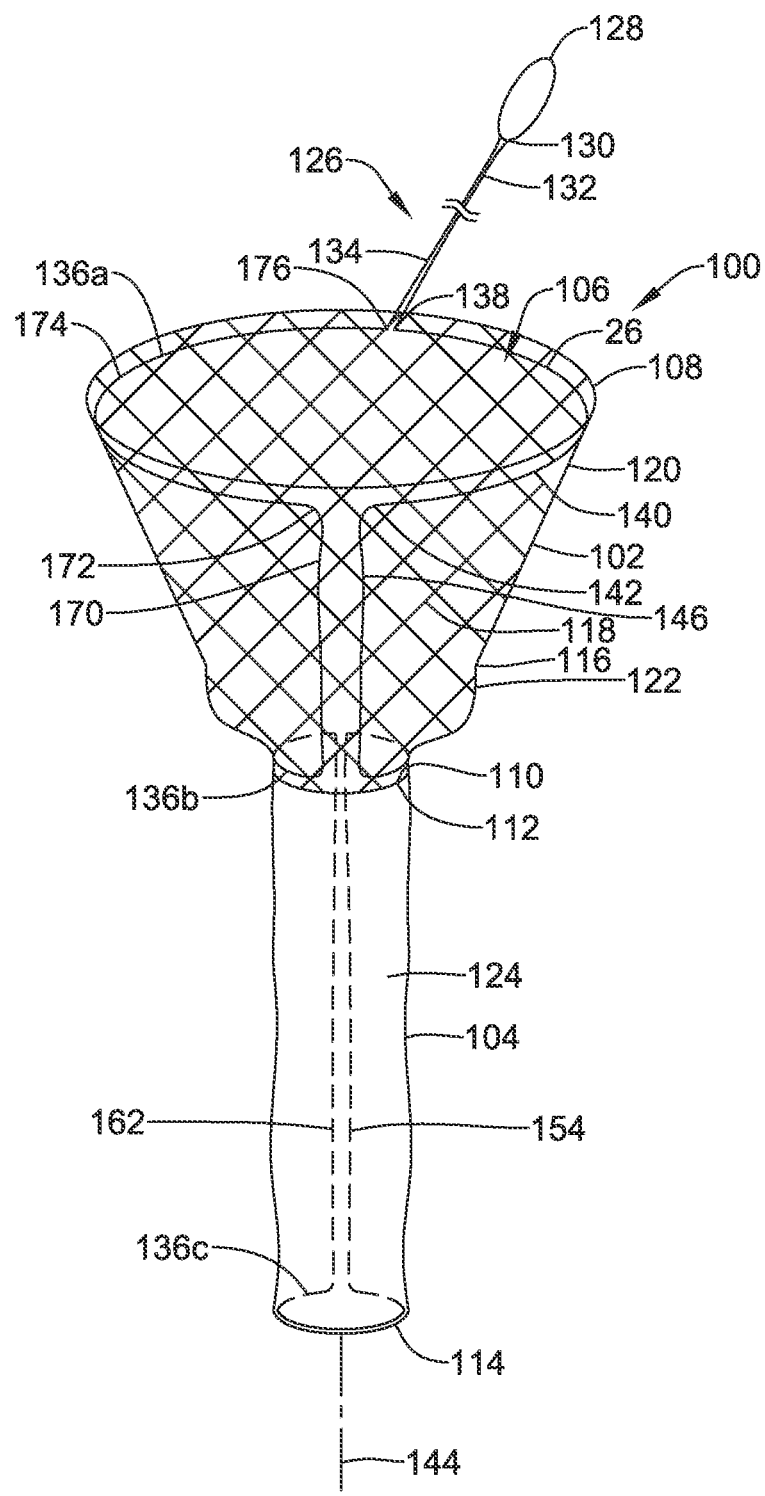
FIG. 5 is a side view of the illustrative implant of FIG. 4 in a first collapsed configuration.
Figure 6:
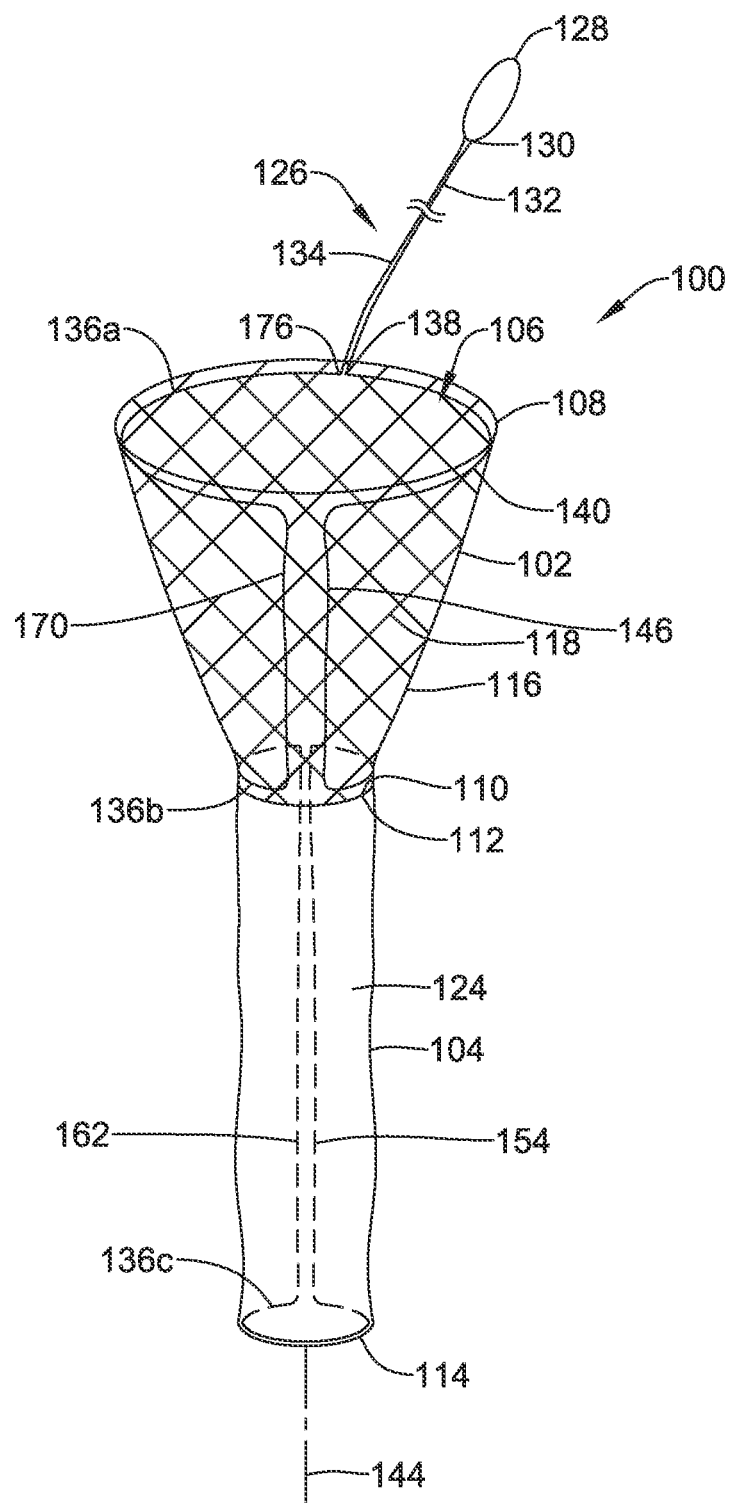
FIG. 6 is a side view of the illustrative implant of FIG. 4 in a second collapsed configuration.

To collapse the implant 100, the retrieval suture loop 128, or the first suture loop 136*a* in the absence of the retrieval suture loop 128, may be pulled or otherwise actuated in a proximal direction. It is contemplated that the direction of actuation (e.g., proximal or distal) required to actuate the suture 126 may be dependent on the direction in which the suture 126 is interwoven with the stent frame 118. As the retrieval suture loop 128, or the first suture loop 136*a* in the absence of the retrieval suture loop 128, is actuated, the suture loops 136 begin to constrain or reduce the diameter of the implant 100, as shown in FIG. 5, which illustrates a side view of the illustrative implant 100 during suture 126 actuation. The distal suture loop 136*c* may be constrained first, causing the distal end 114 of the sleeve 124 to collapse or reduce in diameter before the first end 108. Continued actuation of the retrieval suture loop 128 may cause first end 108 of the implant 100 to also be reduced in diameter, as shown in FIG. 6. It is contemplated that the intermediate suture loop 136*b* may not be actuated until the slack is removed from the preceding longitudinally extending suture loop 136*c* and the suture connection links 154, 162 are drawn taut to apply a force to the next suture loop 136*b*. Similarly, it is contemplated that the proximal suture loop 136*a* may not be actuated until the slack is removed from the preceding longitudinally extending suture loop 136*b* and the suture connection links 146, 170 are drawn taut to apply a force to the next suture loop 136*a*. Such a configuration may allow the sleeve 124 to be retracted into the stent 116 for removal. However, this is not required. In some instances, the connection links 154, 162 and the connection links 146, 170 may have a length such that the suture loops 136 simultaneously (or approximately simultaneously) constrain the implant 100 along its length.

Figure 7A:
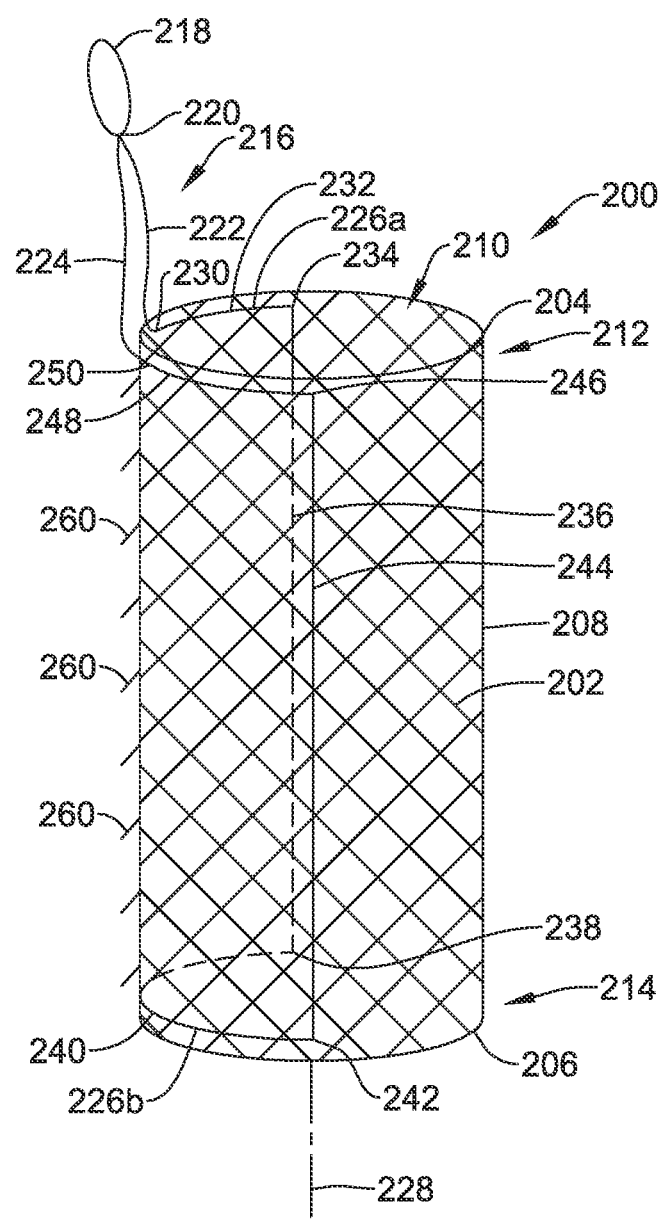
FIG. 7A is a side view of another illustrative implant with a retrieval suture in a first configuration.
Figure 7B:
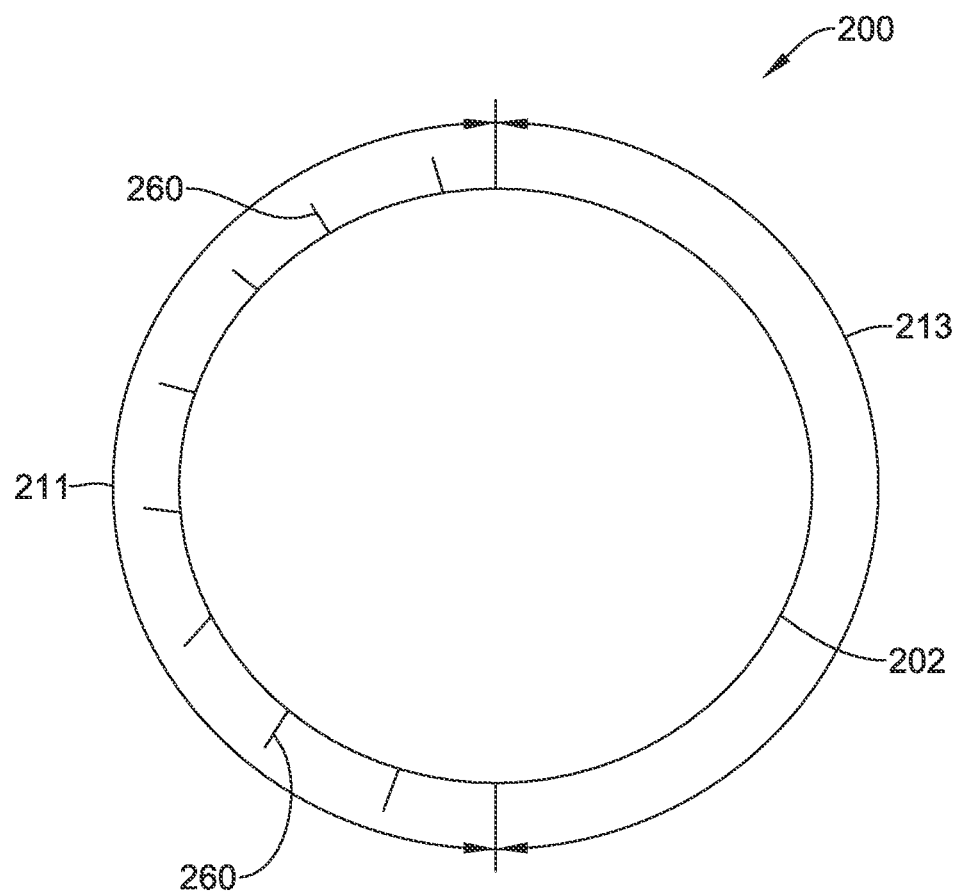
FIG. 7B is a top end view of the illustrative implant of FIG. 7A.

FIG. 7A illustrates a side view of another illustrative endoluminal implant or stent 200. FIG. 7B is a top end view of the illustrative endoluminal implant 200 of FIG. 7A. In some instances, the stent 200 may be formed from an elongated tubular stent frame 202. While the stent 200 is described as generally tubular, it is contemplated that the stent 200 may take any cross-sectional shape desired. The stent 200 may have a first, or proximal end 204, a second, or distal end 206, and an intermediate region 208 disposed between the first end 204 and the second end 206. The stent 200 may include a lumen 210 extending from a first opening adjacent the first end 204 to a second opening adjacent to the second end 206 to allow for the passage of food, fluids, etc.

The stent 200 may be expandable from a first radially collapsed configuration (not explicitly shown) to a second radially expanded configuration. In some cases, the stent 200 may be deployed to a configuration between the collapsed configuration and a fully expanded configuration. The stent 200 may be structured to extend across a stricture and to apply a radially outward pressure to the stricture in a lumen to open the lumen and allow for the passage of foods, fluids, air, etc.

The stent frame 202 may have a woven structure, fabricated from a number of filaments. In some embodiments, the stent frame 202 may be braided with one filament. In other embodiments, the stent frame 202 may be braided with several filaments, as is found, for example, in the WALLFLEX®, WALLSTENT®, and POLYFLEX® stents, made and distributed by Boston Scientific Corp. In another embodiment, the stent frame 202 may be knitted, such as the ULTRAFLEX™ stents made by Boston Scientific Corp. In yet another embodiment, the stent frame 202 may be of a knotted type, such the PRECISION COLONIC™ stents made by Boston Scientific Corp. In still another embodiment, the stent frame 202 may be laser cut, such as the EPIC™ stents made by Boston Scientific Corp.

It is contemplated that the stent 200 can be made from a number of different materials such as, but not limited to, metals, metal alloys, shape memory alloys and/or polymers, as desired, enabling the stent 200 to be expanded into shape when accurately positioned within the body. In some instances, the material may be selected to enable the stent 200 to be removed with relative ease as well. For example, the stent 200 can be formed from alloys such as, but not limited to, Nitinol and ELGILOY®. Depending on the material selected for construction, the stent 200 may be self-expanding (i.e., configured to automatically radially expand when unconstrained). In some embodiments, fibers may be used to make the stent 200, which may be composite fibers, for example, having an outer shell made of Nitinol having a platinum core. It is further contemplated the stent 200 may be formed from polymers including, but not limited to, polyethylene terephthalate (PET). In some embodiments, the stent 200 may be self-expanding while in other embodiments, the stent 200 may be expand by an expansion device (such as, but not limited to a balloon inserted within the lumen 210 of the stent 200). As used herein the term "self-expanding" refers to the tendency of the stent to return to a preprogrammed diameter when unrestrained from an external biasing force (for example, but not limited to a delivery catheter or sheath). The stent 200 may include a one-way valve, such as an elastomeric slit valve or duck bill valve, positioned within the lumen 210 thereof to prevent retrograde flow of gastrointestinal fluids.

In some instances, in the radially expanded configuration, the stent 200 may include a first end region 212 proximate the proximal end 204 and a second end region 214 proximate the second end 206. In some embodiments, the first end region 212 and the second end region 214 may include retention features or anti-migration flared regions (not explicitly shown) having enlarged diameters relative to the intermediate portion 208. The anti-migration flared regions, which may be positioned adjacent to the first end 204 and the second end 206 of the stent 200, may be configured to engage an interior portion of the walls of the esophagus, stomach or other body lumen. In some embodiments, the retention features, or flared regions may have a larger diameter than the cylindrical intermediate region 208 of the stent 200 to prevent the stent 200 from migrating once placed in the esophagus, stomach, or other body lumen. It is contemplated that a transition from the cross-sectional area of the intermediate region 208 to the retention features or flared regions may be gradual, sloped, or occur in an abrupt step-wise manner, as desired. In other embodiments, the stent 200 may have a uniform diameter from the proximal end 204 to the distal end 206, as shown in FIG. 7A.

It is contemplated that the stent 200 can be made from a number of different materials such as, but not limited to, metals, metal alloys, shape memory alloys and/or polymers, as desired, enabling the stent 200 to be expanded into shape when accurately positioned within the body. In some instances, the material may be selected to enable the stent 200 to be removed with relative ease as well. For example, the stent 200 can be formed from alloys such as, but not limited to, Nitinol and ELGILOY®. Depending on the material selected for construction, the stent 200 may be self-expanding or require an external force to expand the stent 200. In some embodiments, composite filaments may be used to make the stent 200, which may include, for example, an outer shell or cladding made of Nitinol and a core formed of platinum or other radiopaque material. It is further contemplated the stent 200 may be formed from polymers including, but not limited to, polyethylene terephthalate (PET). In some instances, the filaments of the stent 200, or portions thereof, may be bioabsorbable or biodegradable, while in other instances the filaments of the stent 200, or portions thereof, may be biostable.

The implant 200 may be may be entirely, substantially or partially, covered with a polymeric covering, such as a coating (not explicitly shown). The covering may be disposed on an inner surface and/or outer surface of the implant 200, as desired. When so provided a polymeric covering may reduce or eliminate tissue ingrowth and/or reduce food impaction.

The implant 200 may further include a retrieval suture 216. The suture 216 may include a retrieval suture loop 218 which may be configured to be grasped by forceps or other tool during a clinical procedure for stent removal and or repositioning. In some cases, the retrieval suture loop 218 may be formed by tying a knot 220 between, or otherwise coupling (e.g., heat bonding, adhesive, etc.) a first end 222 and a second end 224 of the retrieval suture. In other embodiments, the retrieval suture loop 218 may be formed at either the first end 222 or the second end 224 of the retrieval suture 216. In such an instance, the end 222, 224 free from the retrieval suture loop 218 may be coupled to the stent 200 or the opposing end 222, 224 of the retrieval suture 216, although this is not required.

The suture 216 may be interwoven with the stent frame 202 at intervals along a length of the implant 200 to create a plurality of suture loops 226a, 226b (collectively, 226). While the illustrative implant 200 is shown and described has having two suture loops 226, it is contemplated that the implant 200 may include more than two suture loops 226, as desired. For example, the implant 200 may include three, four, five, or more suture loops 226. It is contemplated that the suture loops 226 may be positioned at regular or even intervals throughout the overall length of the implant 200. However, in other embodiments, the suture loops 226 may be positioned at eccentric or uneven intervals along the length of the implant 200, as desired. In some embodiments, one, two or more, or all of the suture loops 226 may extend less than an entire circumference or less than 360° of the circumference of the stent frame 202. In the illustrative embodiment, the suture loops 226 may extend about or have an arc length of 180° or about half of the circumference of the stent frame 202. In other embodiments, one, two or more, or all of the suture loops 226 may extend or have an arc length of less than 360° about the circumference of the stent frame 202. In some embodiments, one or more of the suture loops 226 may extend 350° or less, 300° or less, 270° or less, 225° or less, 180° or less, or 135° or less around the circumference of the stent frame 202. In yet other embodiments, one, two or more, or all of the suture loops may extend about 360° or more than 360° about the circumference of the stent frame 202, as desired. It is further contemplated that all of the suture loops 226 need not have the same arc length. For example, a first suture loop may extend about 180° while a second suture loop may extend about 270°. This is just one example. It is contemplated that the size and shape of each of the suture loops 226 may be selected to customize containment of the stent 200. For example, if barbs or protrusions 260 are provided on one side of the stent 200, it may be desirable to constrain the side of the stent 200 having the barbs or protrusions 260 in order to disengage the barbs or protrusions 260 from a luminal wall of a body lumen prior to removing or repositioning the stent 200. In some instances, the barbs or protrusions 260 may be positioned only around a portion of the circumference of the stent 200, leaving a remainder of the circumference of the stent 200 devoid of any barbs or protrusions. For example, the barbs or protrusions 260 may be positioned only around 270° or less, 225° or less, 180° or less, or 135° or less of the circumference of the stent 200. Accordingly, the suture loops 226 may extend around the portion of the circumference of the stent 200 including the barbs or protrusions 260, while not extending around the remainder of the circumference of the stent 200, which is devoid of barbs or protrusions.

In the illustrative embodiment, the stent 200 may have a first circumferential region 211 of the circumference of the stent 200 which is directly manipulated by the suture 216 and a second circumferential region 213 of the circumference of the stent 200 which is not directly manipulated by the suture 216. The first circumferential region 211 of the circumference of the stent 200 may correspond to the portion of the circumference of the stent 200 having the barbs or protrusions 260, while the second circumferential region 213 of the circumference of the stent 200 may correspond to the portion of the circumference of the stent 200 devoid of any barbs or protrusions. When the stent 200 is in the unconstrained configuration (e.g., as shown in FIGS. 7A and 7B), the first circumferential region 211 may have a first arc length and the second circumferential region 213 may have a second arc length. When the suture loops 226 extend about 180° about the circumference, the arc lengths of the first and second circumferential regions 211, 213 may be approximately equal, although this is not required. It should be understood that the arc length of the first and second circumferential regions 211, 213 correspond to the circumferential distance the suture loops 226 extend about the circumference of the stent 200.

The suture loops 226 may be formed from a single unitary suture 216. It is contemplated that the suture 216 may be interwoven with the stent frame 202 such that the suture loops 226 may be constrained in a predetermined sequential order. In some cases, the proximal loop 226a may not extend in a continuous loop. Rather, the proximal loop 226a may be broken into sections by longitudinally extending interconnecting segments 46, 58 which extend between the proximal loop 226a and the distal loop 226b.

The suture 216 may be interwoven with the stent frame 202 by threading one of the ends 222, 224 around the proximal end 204 of the implant 200 beginning at a first circumferential location 230 and moving (e.g., threading) in a first direction. In the illustrative example, the suture 216 is described as initially being threaded in a clockwise direction. However, the reverse configuration in which the suture is initially threaded in a counterclockwise direction is also contemplated. The suture 216 may be threaded around about one quarter of the circumference (or about 90°) of the implant 200 such that a first segment 232 of the suture 216 extends between the first circumferential location 230 and a second circumferential location 234. The first and second circumferential locations 230, 234 may be positioned at a similar longitudinal distance (e.g., in a direction extending generally parallel to the longitudinal axis 228 of the implant 200) from the first end 204 of the implant 200. In some cases, the suture 216 may be threaded such that it is interwoven with the stent frame 202 such that a portion of the suture 216 is within the lumen 210 of the implant 200 and a portion of the suture 216 is positioned along an exterior surface of the implant 200 (e.g., such that it will be in contact with a vessel lumen when the implant 200 is deployed within the body). At the second circumferential location 234, the suture 216 may be threaded along a length of implant 200 in a direction towards the second end 206 such that a second longitudinally extending interconnecting segment 236 of the suture 216 extends along a length of the implant 200 in a generally linear direction. The length of the second segment 236 of the suture 216 may vary depending on the application. For example, some implants 200 may include radially extending barbs or protrusions 260 configured to engage a body tissue. The second segment 236 may be configured to extend along a length equal to or greater to a length of the implant 200 including the radially extending barbs or protrusions 260. This is just one example. Other features of the implant 200, such as, but not limited to, the length of the implant 200 may be used to determine the length of the second segment 236 of the suture 216.

The second segment 236 of the suture 216 may extend from the second circumferential location 234 to a third circumferential location 238. The second circumferential location and the third circumferential location 238 may be at similar radial points about the circumference of the implant 200 but spaced a distance along the length thereof. At the third circumferential location 238, a third segment 240 of the suture 216 may be threaded radially about the circumference of the implant 200 in a second direction (e.g., counterclockwise), opposite to the first direction. The third segment 240 may extend between the third circumferential location 238 and a fourth circumferential location 242 to form a suture loop 226b. The arc length of the third segment 240 may be less than 360° of the circumference. In some cases, the arc length of the third segment 240 may be in the range of 350° or less, 300° or less, 270° or less, 225° or less, 180° or less, 135° or less, etc. of the circumference. The third circumferential location 238 and the fourth circumferential location 242 may be radially spaced from one another by, for example, 10° or more, 60° or more, 90° or more, 135° or more, 180° or more, 225° or more, etc.

At the fourth circumferential location 242, the suture 216 may be threaded along a length of implant 200 in a direction towards the first end 204 such that a fourth longitudinally extending interconnecting segment 244 of the suture 216 extends along a length of the implant 200 in a direction to the longitudinal axis 228. The length of the fourth segment 244 of the suture 216 may be about the same length as the second segment 236 of the suture 216. The fourth segment 244 of the suture 216 may extend between the fourth circumferential location 242 and a fifth circumferential location 246. In some cases, the second and/or fourth segments 236, 244 of the suture 216 may not be interwoven with the stent body 202 but rather extend along an inner or outer surface of the stent body 202. In some embodiments, the first, second, and fifth circumferential locations 230, 234, 246 may be positioned at a similar longitudinal distance (e.g., in a direction extending generally parallel to the longitudinal axis 228 of the implant 200) from the first end 204 of the implant 200.

From the fifth circumferential location 246, the suture 216 may be threaded through the stent body 202 in the first direction (e.g., away from the first segment 232) to form a fifth segment 248 of the suture 216. The fifth segment 248 of the suture 216 may be threaded through the stent body 202 to a sixth circumferential location 250 and/or until it meets the first circumferential location 230 (e.g., the starting point) to form the proximal loop 226a. As described above, the proximal suture loop 226a may be formed of discontinuous or broken segments 232, 248. In some embodiments, the fifth segment 248 ceases to be interwoven with the stent body 202 before the suture 216 reaches the first circumferential location 230. For example, the first circumferential location 230 may be radially spaced from the sixth circumferential location 250 may be radially spaced from one another by, for example, 1° or less, 5° or less, 10° or less, 20° or less, etc. A first end 222 of the suture 216 may extend from the first circumferential location 230 and the second end 224 of the suture 216 may extend from the sixth circumferential location 250. The ends 222, 224 of the suture 216 may be tied to form a knot 220, glued, and the knot 220 subsequently cured.

It is contemplated that in embodiments where it is desired for the suture 216 to include suture loops 226 which extend around less than the entire circumference, as shown, the suture 216 may be initially threaded about half the length of the desired final arc length. For example, if the finished suture loop 226 is to extend about 180° about the circumference of the implant 200, the suture 216 may be initially threaded about 90° around the circumference before being threaded down a length of the implant 200, as shown and described.

Figure 8A:
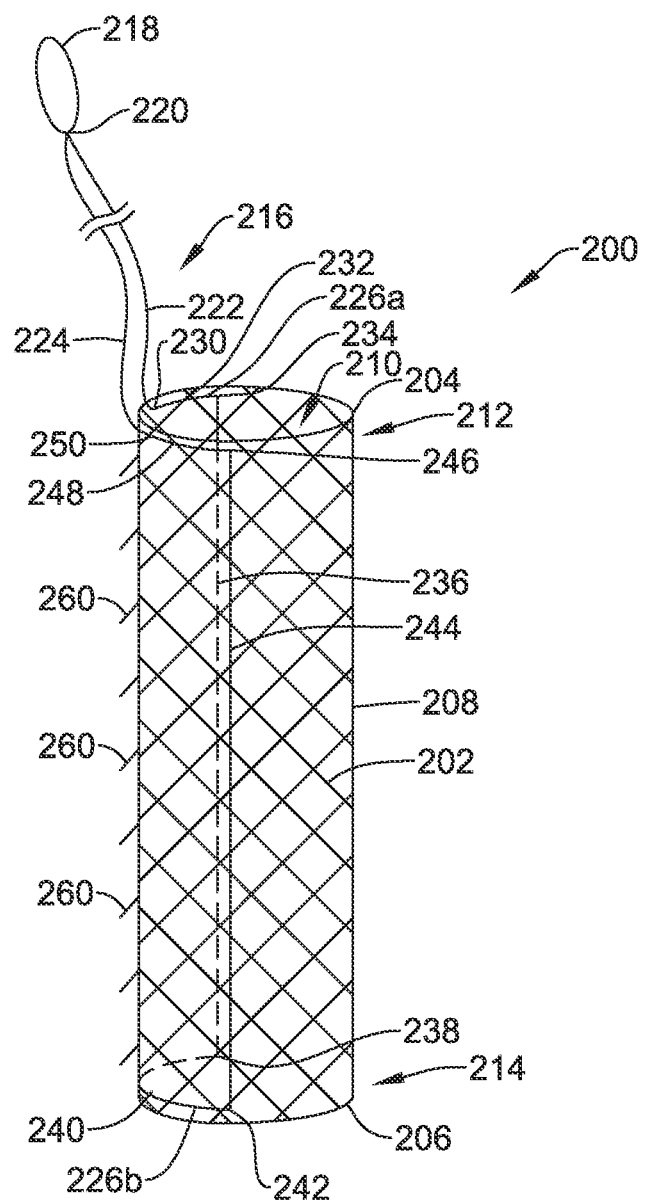
FIG. 8A is a side view of the illustrative implant of FIG. 7A in a first collapsed configuration.

To collapse the implant 200, the retrieval suture loop 218, or the first suture loop 226a in the absence of the retrieval suture loop 218, may be pulled or otherwise actuated in a proximal direction. It is contemplated that the direction of actuation (e.g., proximal or distal) required to actuate the suture 216 may be dependent on the direction in which the suture 216 is interwoven with the stent frame 202. As the retrieval suture loop 218, or the first suture loop 226a in the absence of the retrieval suture loop 218, is actuated, the suture loops 226 begin to constrain or reduce the diameter of the implant 200, as shown in FIG. 8A, which illustrates a side view of the illustrative implant 200 during suture 216 actuation. As the suture loops 226 are positioned to one side (e.g., circumferential region 211) of the implant 200, the implant 200 may constrain or collapse more significantly or to a greater extent adjacent to the suture loops 226. The distal or second suture loop 226b may be constrained first, causing the distal end portion 206 of the stent body 202 to collapse or reduce in diameter before the first end 204. Continued actuation of the retrieval suture loop 218 may cause first end 204 of the implant 200 to also be reduced in diameter, as shown in FIG. 8A. It is contemplated that the proximal or first suture loop 226a may not be actuated until the slack is removed from the preceding longitudinally extending suture loop 226b and the suture connection links 236, 244 are drawn taut to apply a force to the next suture loop 226a. However, this is not required. In some instances, the connection links 236, 244 may have a length such that the suture loops 226 simultaneously (or approximately simultaneously) constrain the implant 200 along its length.

Figure 8B:
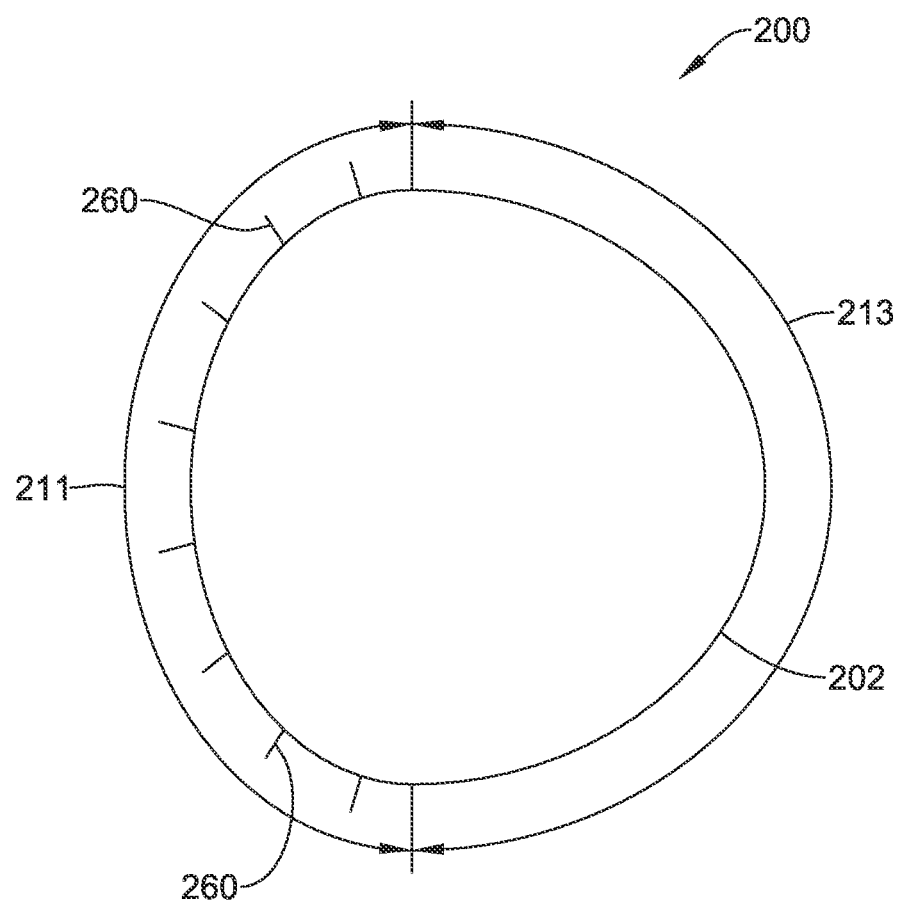
FIG. 8B is a top end view of the illustrative implant of FIG. 8A.

It is contemplated that the orientation of the suture loops 226 may preferentially collapse the first circumferential region 211 of the stent 200 which includes the barbs or projections 260. This may cause the arc length of the first circumferential region 211 to shorten (relative to the unconstrained configuration) as the circumferential region 211 is collapsed, as shown in FIG. 8B, which illustrates a top view of the illustrative stent of FIG. 8A. Constrainment and shortening of the arc length of the first circumferential region 211 may disengage the barbs or projections 260 from the luminal wall of a body lumen to facilitate removal of the stent 200 from the body lumen and/or facilitate repositioning of the stent 200 in the body lumen. In some cases, constrainment of the first circumferential region 211 may cause some deformation and/or constrainment of the second circumferential region 213. In some cases, the second circumferential region 213 may assume a more oblong shape as the first circumferential region 211 is constrained, as shown in FIG. 8B. In some cases, the arc length of the second circumferential region 211 may remain approximately constant, may slightly increase or may slightly decrease relative to the unconstrained configuration.

Figure 9:
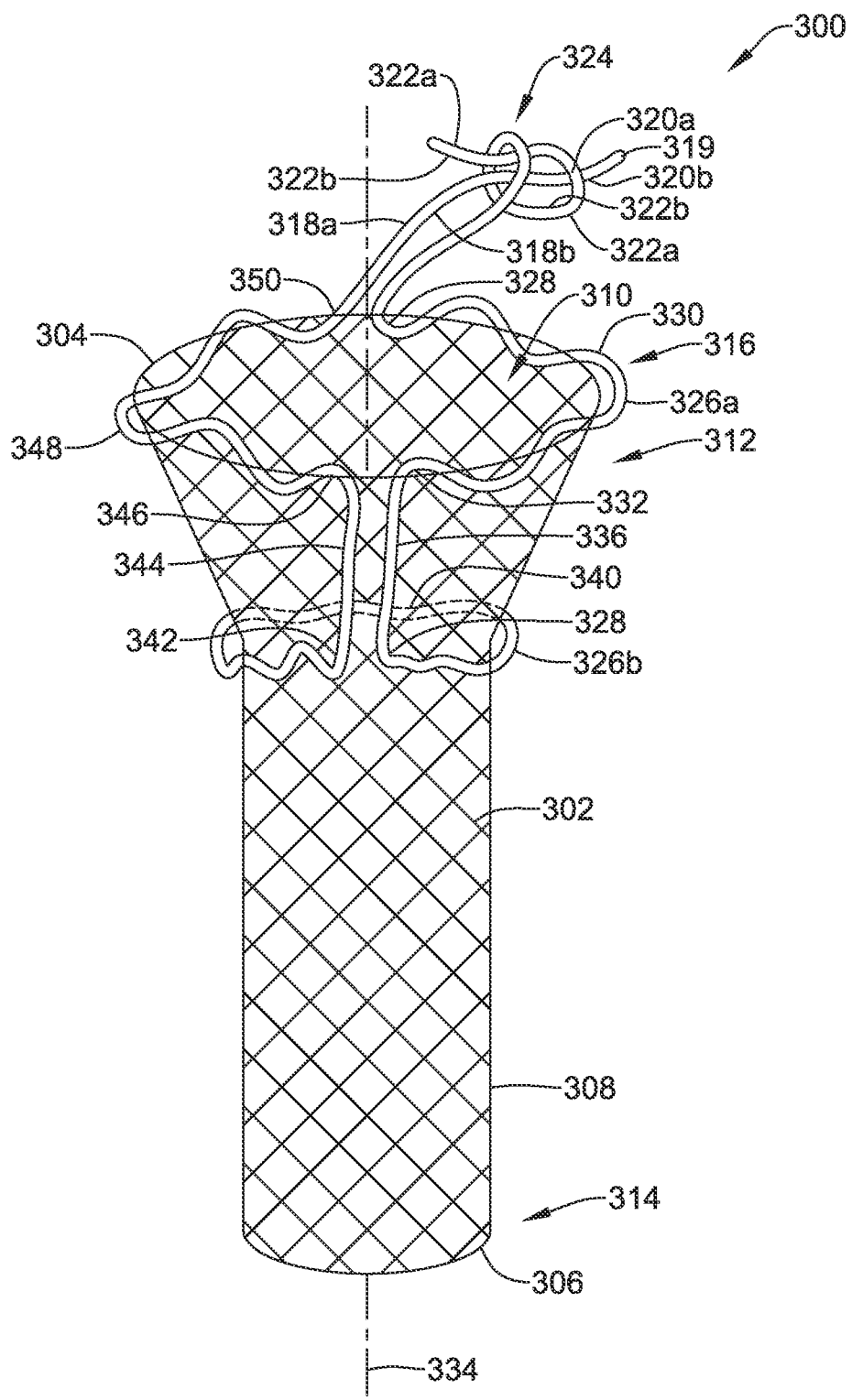
FIG. 9 is a side view of another illustrative implant with a retrieval suture in a first configuration.

FIG. 9 illustrates a side view of an illustrative endoluminal implant or stent 300. In some instances, the stent 300 may be formed from an elongated tubular stent frame 302. While the stent 300 is described as generally tubular, it is contemplated that the stent 300 may take any cross-sectional shape desired. The stent 300 may have a first, or proximal end 304, a second, or distal end 306, and an intermediate region 308 disposed between the first end 304 and the second end 306. The stent 300 may include a lumen 310 extending from a first opening adjacent the first end 304 to a second opening adjacent to the second end 306 to allow for the passage of food, fluids, etc.

The stent 300 may be expandable from a first radially collapsed configuration (not explicitly shown) to a second radially expanded configuration. In some cases, the stent 300 may be deployed to a configuration between the collapsed configuration and a fully expanded configuration. The stent 300 may be structured to extend across a stricture and to apply a radially outward pressure to the stricture in a lumen to open the lumen and allow for the passage of foods, fluids, air, etc.

The stent frame 302 may have a woven structure, fabricated from a number of filaments. In some embodiments, the stent frame 302 may be braided with one filament. In other embodiments, the stent frame 302 may be braided with several filaments, as is found, for example, in the WALL-FLEX®, WALLSTENT®, and POLYFLEX® stents, made and distributed by Boston Scientific Corp. In another embodiment, the stent frame 302 may be knitted, such as the ULTRAFLEX™ stents made by Boston Scientific Corp. In yet another embodiment, the stent frame 302 may be of a knotted type, such the PRECISION COLONIC™ stents made by Boston Scientific Corp. In still another embodiment, the stent frame 302 may be laser cut, such as the EPIC™ stents made by Boston Scientific Corp.

It is contemplated that the stent 300 can be made from a number of different materials such as, but not limited to, metals, metal alloys, shape memory alloys, and/or polymers, as desired, enabling the stent 300 to be expanded into shape when accurately positioned within the body. In some instances, the material may be selected to enable the stent 300 to be removed with relative ease as well. For example, the stent 300 can be formed from alloys such as, but not limited to, Nitinol and ELGILOY®. Depending on the material selected for construction, the stent 300 may be self-expanding (i.e., configured to automatically radially expand when unconstrained). In some embodiments, fibers may be used to make the stent 300, which may be composite fibers, for example, having an outer shell made of Nitinol having a platinum core. It is further contemplated the stent 300 may be formed from polymers including, but not limited to, polyethylene terephthalate (PET). In some embodiments, the stent 300 may be self-expanding while in other embodiments, the stent 300 may be expand by an expansion device (such as, but not limited to a balloon inserted within the lumen 310 of the stent 300). As used herein the term "self-expanding" refers to the tendency of the stent to return to a preprogrammed diameter when unrestrained from an external biasing force (for example, but not limited to a delivery catheter or sheath). The stent 300 may include a one-way valve, such as an elastomeric slit valve or duck bill valve, positioned within the lumen 310 thereof to prevent retrograde flow of gastrointestinal fluids.

In some instances, in the radially expanded configuration, the stent 300 may include a first end region 312 proximate the proximal end 304 and a second end region 314 proximate the second end 306. In some embodiments, the first end region 312 and the second end region 314 may include retention features or anti-migration flared regions (not explicitly shown at the second end region 314) having enlarged diameters relative to the intermediate portion 308. The anti-migration flared regions, which may be positioned adjacent to the first end 304 and the second end 306 of the stent 300, may be configured to engage an interior portion of the walls of the esophagus, stomach or other body lumen. In some embodiments, the retention features, or flared regions may have a larger diameter than the cylindrical intermediate region 308 of the stent 300 to prevent the stent 300 from migrating once placed in the esophagus, stomach, or other body lumen. It is contemplated that a transition from the cross-sectional area of the intermediate region 308 to the retention features or flared regions may be gradual, sloped, or occur in an abrupt step-wise manner, as desired. In other embodiments, the stent 300 may have a uniform diameter from the proximal end 304 to the distal end 306.

It is contemplated that the stent 300 can be made from a number of different materials such as, but not limited to, metals, metal alloys, shape memory alloys and/or polymers, as desired, enabling the stent 300 to be expanded into shape when accurately positioned within the body. In some instances, the material may be selected to enable the stent 300 to be removed with relative ease as well. For example, the stent 300 can be formed from alloys such as, but not limited to, Nitinol and ELGILOY®. Depending on the material selected for construction, the stent 300 may be self-expanding or require an external force to expand the stent 300. In some embodiments, composite filaments may be used to make the stent 300, which may include, for example, an outer shell or cladding made of Nitinol and a core formed of platinum or other radiopaque material. It is further contemplated the stent 300 may be formed from polymers including, but not limited to, polyethylene terephthalate (PET). In some instances, the filaments of the stent 300, or portions thereof, may be bioabsorbable or biodegradable, while in other instances the filaments of the stent 300, or portions thereof, may be biostable.

The implant 300 may be may be entirely, substantially or partially, covered with a polymeric covering, such as a coating (not explicitly shown). The covering may be disposed on an inner surface and/or outer surface of the implant 300, as desired. When so provided a polymeric covering may reduce or eliminate tissue ingrowth and/or reduce food impaction.

The implant 300 may further include a retrieval suture 316. The retrieval suture 316 may be formed from a first suture strand 318a and a second suture strand 318b (collectively, 318). The suture strands 318a, 318b may be a single strand which has been doubled back on itself, as shown at 319 in FIG. 9. It is contemplated that in such an instances, the retrieval suture 316 may be doubled back on itself prior to interweaving the retrieval suture 316 with the implant 300. In other embodiments, the suture strands 318a, 318b separate strands extending side by side. While the retrieval suture 316 is described as having two suture strands 318, it is contemplated that the retrieval sutures 316 may include fewer than two strands or more than two strands, as desired. The region 319 where the suture 316 is doubled back on itself may define a first end 320a, 320b of the suture strands 318 while the free ends of retrieval suture 316 may form a second end 322a, 322b of each strand 318a, 318b. The first end 320a, 320b (collectively, 320) of each strand 318a, 318b may be knotted with the second end 322a, 322b (collectively, 322) of each strand 318a, 318b to form a knot 324. In some cases, the knot 324 may be a slip knot or other knot which allows either the first or second ends 320, 322 to be grasped and actuated by forceps or other tool during a clinical procedure for stent removal and or repositioning. It is contemplated that the use of a sliding knot 324 may reduce or eliminate breakage of the retrieval suture 316 during removal or repositioning of the implant 300.

The retrieval suture 316 may be interwoven with the stent frame 302 at intervals along a length of the implant 300 to create a plurality of suture loops 326a, 326b (collectively, 326). While the illustrative implant 300 is shown and described has having two suture loops 326, it is contemplated that the implant 300 may include more than two suture loops 326, as desired. For example, the implant 300 may include three, four, five, or more suture loops 326. It is contemplated that the suture loops 326 may be positioned at regular or even intervals throughout the overall length of the implant 300. However, in other embodiments, the suture loops 326 may be positioned at eccentric or uneven intervals along the length of the implant 300, as desired. It is contemplated that the suture loops 326 may be positioned to facilitate retrieval, repositioning, and/or reshaping of the stent 300. For example, in a stent 300 having two or more flared or enlarged regions, as in the AXIOS® stent made and distributed by Boston Scientific Corp., a first retrieval suture loop 326a may be positioned adjacent to the first flare and a second retrieval suture loop 326b may be positioned adjacent to the second flare.

In some embodiments, one, two or more, or all of the suture loops 326 may extend entirely around the circumference (e.g., 360°) of the stent frame 302. In other embodiments, one, two or more, or all of the suture loops 326 may extend less than 360° about the circumference of the stent frame 302. In some embodiments, one or more of the suture loops 326 may extend 350° or less, 300° or less, 270° or less, 225° or less, 180° or less, 135° or less, etc. In yet other embodiments, one, two or more, or all of the suture loops may extend more than 360° about the circumference of the stent frame 302.

As described above, the suture loops 326 may be formed from two or more suture strands 318. It is contemplated that the suture strands 318 may be interwoven with the stent frame 302 such that the suture loops 326 may be constrained in a predetermined sequential order. In some cases, the proximal loop 326a may not extend in a continuous loop. Rather, the proximal loop 326a may be broken into sections by longitudinally extending interconnecting segments 336, 344 which extend between the proximal loop 326a and the distal loop 326b.

The suture strands 318 may be interwoven with the stent frame 302 by threading one of the ends 320, 322 around the proximal end 304 of the implant 300 beginning at a first circumferential location 328 and moving (e.g., threading) in a first direction. In the illustrative example, the suture 316 is described as initially being threaded in a clockwise direction. However, the reverse configuration in which the suture is initially threaded in a counterclockwise direction is also contemplated. The suture 316 may be threaded around about one half of the circumference of the implant 300 such that a first segment 330 of the suture 316 extends between the first circumferential location 328 and a second circumferential location 332. The first and second circumferential locations 328, 332 may be positioned at a similar longitudinal distance (e.g., in a direction extending generally parallel to the longitudinal axis 334 of the implant 300) from the first end 304 of the implant 300. In some cases, the suture 316 may be threaded such that it is interwoven with the stent frame 302 such that a portion of the suture 316 is within the lumen 310 of the implant 300 and a portion of the suture 316 is positioned along an exterior surface of the implant 300 (e.g., such that it will be in contact with a vessel lumen when the implant 300 is deployed within the body). At the second circumferential location 332, the suture 316 may be threaded along a length of implant 300 in a direction towards the second end 306 such that a second longitudinally extending interconnecting segment 336 of the suture 316 extends along a length of the implant 300 in a generally linear direction. The length of the second segment 336 of the suture 316 may vary depending on the application. For example, some implants 300 may include radially extending quills (not explicitly shown) configured to engage a body tissue. The second segment 336 may be configured to extend along a length equal to or greater to a length of the implant 300 including the radially extending quills. This is just one example. Other features of the implant 300, such as, but not limited to, the length of the implant 300 may be used to determine the length of the second segment 336 of the suture 316.

The second segment 336 of the suture 316 may extend from the second circumferential location 332 to a third circumferential location 338. The second circumferential location 332 and the third circumferential location 338 may be at similar radial points about the circumference of the implant 300 but spaced a distance along the length thereof. At the third circumferential location 338, a third segment 340 of the suture 316 may be threaded radially about the circumference of the implant 300 in a second direction (e.g., counterclockwise), opposite to the first direction. The third segment 340 may extend between the third circumferential location 338 and a fourth circumferential location 342 to form a suture loop 326b. In some embodiments, the third circumferential location 338 and the fourth circumferential location 342 may be at substantially the same radial point about the circumference of the implant 300 such that the suture loop 326b extends substantially or entirely 360° about the circumference of the implant 300. In other embodiments the third circumferential location 338 and the fourth circumferential location 342 may be radially spaced from one another by, for example, 1° or less, 5° or less, 10° or less, 20° or less, etc.

At the fourth circumferential location 342, the suture 316 may be threaded along a length of implant 300 in a direction towards the first end 304 such that a fourth longitudinally extending interconnecting segment 344 of the suture 316 extends along a length of the implant 300 in a direction to the longitudinal axis 334. The length of the fourth segment 344 of the suture 316 may be about the same length as the second segment 336 of the suture 316. The fourth segment 344 of the suture 316 may extend between the fourth circumferential location 342 and a fifth circumferential location 346. In some cases, the second and/or fourth segments 336, 344 of the suture may not be interwoven with the stent body 302 but rather extend along an inner or outer surface of the stent body 302. In some embodiments, the first, second, and fifth circumferential locations 328, 332, 346 may be positioned at a similar longitudinal distance (e.g., in a direction extending generally parallel to the longitudinal axis 334 of the implant 300) from the first end 304 of the implant 300.

From the fifth circumferential location 346, the suture 316 may be threaded through the stent body 302 in the first direction (e.g., away from the first segment 330) to form fifth segment 348 of the suture 316. The fifth segment 348 of the suture 316 may be threaded through the stent body 302 to a sixth circumferential location 350 and/or until it meets the first circumferential location 328 (e.g., the starting point) to form the proximal loop 326a. As described above, the proximal suture loop 326a may be formed of discontinuous or broken segments 330, 348. In some embodiments, the fifth segment 348 ceases to be interwoven with the stent body 302 before the suture 316 reaches the first circumferential location 328. For example, the first circumferential location 328 may be radially spaced from the sixth circumferential location 350 by, for example, 1° or less, 5° or less, 10° or less, 20° or less, etc. In the illustrated example, the second ends 322 of the suture strands 318 may extend from the first circumferential location 328 and the first ends 320 of the suture strands 318 may extend from the sixth circumferential location 350. The ends 320, 322 of the suture 316 may be tied to form a slip knot 324, as described above.

To collapse the implant 300, an end 320, 322 of one of the suture strands 318, may be pulled or otherwise actuated in a proximal direction. It is contemplated that the direction of actuation (e.g., proximal or distal) required to actuate the suture 316 may be dependent on the direction in which the suture 316 is interwoven with the stent frame 302. As the first ends 320 or second ends 322 are actuated, the suture loops 326 begin to constrain or reduce the diameter (not explicitly shown) of the implant 300. The distal or second suture loop 326b may be constrained first, causing the intermediate portion 308 of the stent body 302 to collapse or reduce in diameter before the first end 304. Continued actuation of the sutures strands 318 may cause the first end 304 of the implant 300 to also be reduced in diameter (not explicitly shown). It is contemplated that the proximal or first suture loop 326a may not be actuated until the slack is removed from the preceding longitudinally extending suture loop 326b and the suture connection links 336, 344 are drawn taut to apply a force to the next suture loop 326a. However, this is not required. In some instances, the connection links 336, 344 may have a length such that the suture loops 326 simultaneously (or approximately simultaneously) constrain the implant 300 along its length.

Figure 10:
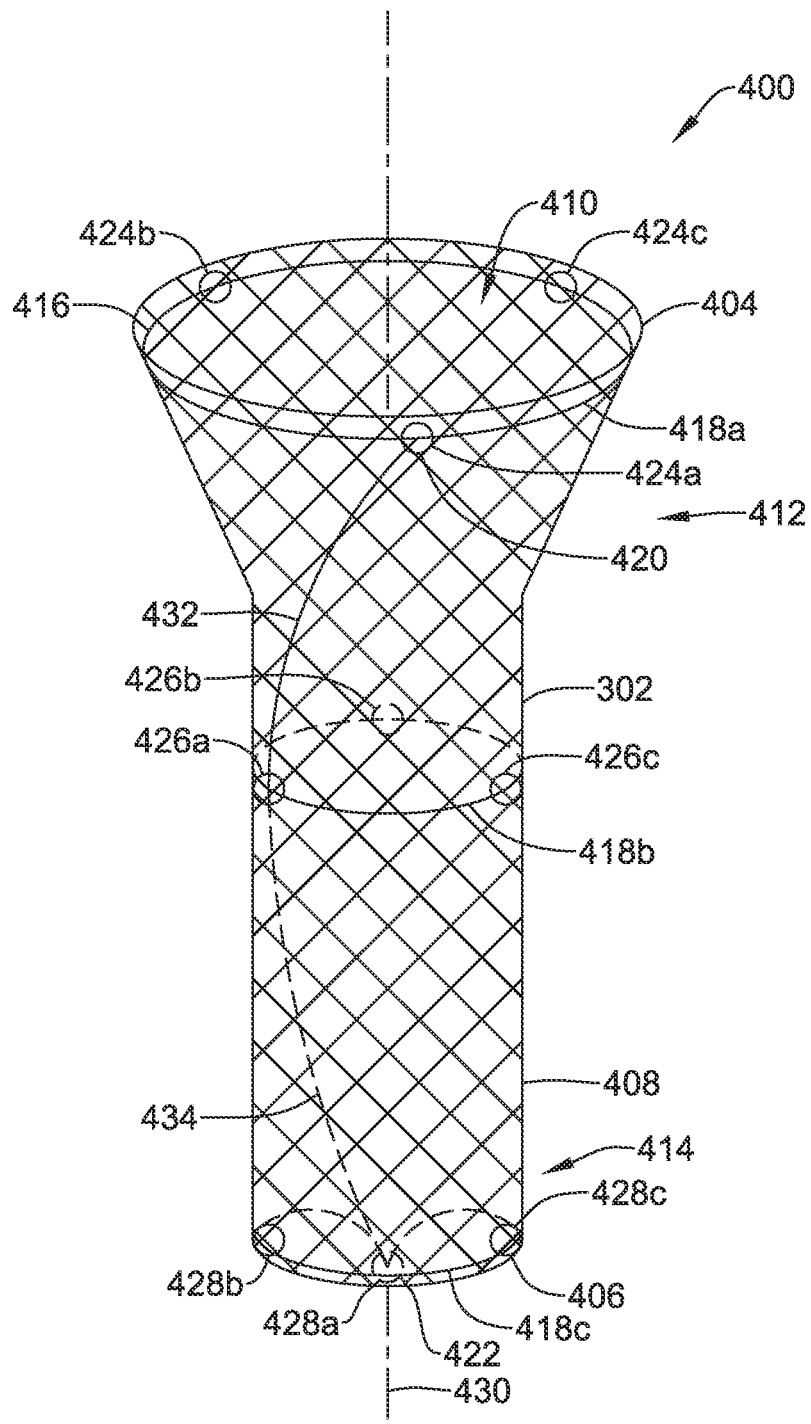
FIG. 10 is a side view of another illustrative implant with a retrieval suture in a first configuration.

FIG. 10 illustrates a side view of an illustrative endoluminal implant or stent 400. In some instances, the stent 400 may be formed from an elongated tubular stent frame 402. While the stent 400 is described as generally tubular, it is contemplated that the stent 400 may take any cross-sectional shape desired. The stent 400 may have a first, or proximal end 404, a second, or distal end 406, and an intermediate region 408 disposed between the first end 404 and the second end 406. The stent 400 may include a lumen 410 extending from a first opening adjacent the first end 404 to a second opening adjacent to the second end 406 to allow for the passage of food, fluids, etc.

The stent 400 may be expandable from a first radially collapsed configuration (not explicitly shown) to a second radially expanded configuration. In some cases, the stent 400 may be deployed to a configuration between the collapsed configuration and a fully expanded configuration. The stent 400 may be structured to extend across a stricture and to apply a radially outward pressure to the stricture in a lumen to open the lumen and allow for the passage of foods, fluids, air, etc.

The stent frame 402 may have a woven structure, fabricated from a number of filaments. In some embodiments, the stent frame 402 may be braided with one filament. In other embodiments, the stent frame 402 may be braided with several filaments, as is found, for example, in the WALL-FLEX®, WALLSTENT®, and POLYFLEX® stents, made and distributed by Boston Scientific Corp. In another embodiment, the stent frame 402 may be knitted, such as the ULTRAFLEX™ stents made by Boston Scientific Corp. In yet another embodiment, the stent frame 402 may be of a knotted type, such the PRECISION COLONIC™ stents made by Boston Scientific Corp. In still another embodiment, the stent frame 402 may be laser cut, such as the EPIC™ stents made by Boston Scientific Corp.

It is contemplated that the stent 400 can be made from a number of different materials such as, but not limited to, metals, metal alloys, shape memory alloys, and/or polymers, as desired, enabling the stent 400 to be expanded into shape when accurately positioned within the body. In some instances, the material may be selected to enable the stent 400 to be removed with relative ease as well. For example, the stent 400 can be formed from alloys such as, but not limited to, Nitinol and ELGILOY®. Depending on the material selected for construction, the stent 400 may be self-expanding (i.e., configured to automatically radially expand when unconstrained). In some embodiments, fibers may be used to make the stent 400, which may be composite fibers, for example, having an outer shell made of Nitinol having a platinum core. It is further contemplated the stent 400 may be formed from polymers including, but not limited to, polyethylene terephthalate (PET). In some embodiments, the stent 400 may be self-expanding while in other embodiments, the stent 400 may be expand by an expansion device (such as, but not limited to a balloon inserted within the lumen 410 of the stent 400). As used herein the term "self-expanding" refers to the tendency of the stent to return to a preprogrammed diameter when unrestrained from an external biasing force (for example, but not limited to a delivery catheter or sheath). The stent 400 may include a one-way valve, such as an elastomeric slit valve or duck bill valve, positioned within the lumen 410 thereof to prevent retrograde flow of gastrointestinal fluids.

In some instances, in the radially expanded configuration, the stent 400 may include a first end region 412 proximate the proximal end 404 and a second end region 414 proximate the second end 406. In some embodiments, the first end region 412 and the second end region 414 may include retention features or anti-migration flared regions (not explicitly shown at the second end region 414) having enlarged diameters relative to the intermediate portion 408. The anti-migration flared regions, which may be positioned adjacent to the first end 404 and the second end 406 of the stent 400, may be configured to engage an interior portion of the walls of the esophagus, stomach or other body lumen. In some embodiments, the retention features, or flared regions may have a larger diameter than the cylindrical intermediate region 408 of the stent 400 to prevent the stent 400 from migrating once placed in the esophagus, stomach, or other body lumen. It is contemplated that a transition from the cross-sectional area of the intermediate region 408 to the retention features or flared regions may be gradual, sloped, or occur in an abrupt step-wise manner, as desired. In other embodiments, the stent 400 may have a uniform diameter from the proximal end 404 to the distal end 406.

It is contemplated that the stent 400 can be made from a number of different materials such as, but not limited to, metals, metal alloys, shape memory alloys and/or polymers, as desired, enabling the stent 400 to be expanded into shape when accurately positioned within the body. In some instances, the material may be selected to enable the stent 400 to be removed with relative ease as well. For example, the stent 400 can be formed from alloys such as, but not limited to, Nitinol and ELGILOY®. Depending on the material selected for construction, the stent 400 may be self-expanding or require an external force to expand the stent 400. In some embodiments, composite filaments may be used to make the stent 400, which may include, for example, an outer shell or cladding made of Nitinol and a core formed of platinum or other radiopaque material. It is further contemplated the stent 400 may be formed from polymers including, but not limited to, polyethylene terephthalate (PET). In some instances, the filaments of the stent 400, or portions thereof, may be bioabsorbable or biodegradable, while in other instances the filaments of the stent 400, or portions thereof, may be biostable.

The implant 400 may be may be entirely, substantially or partially, covered with a polymeric covering, such as a coating (not explicitly shown). The covering may be disposed on an inner surface and/or outer surface of the implant 400, as desired. When so provided a polymeric covering may reduce or eliminate tissue ingrowth and/or reduce food impaction.

The implant 400 may further include a suture 416. The suture 416 may be interwoven with the stent frame 402 at intervals along a length of the implant 400 to create a plurality of suture loops 418a, 418b, 418c (collectively, 418). While the illustrative implant 400 is shown and described has having three suture loops 418, it is contemplated that the implant 400 may include fewer than three or more than three suture loops 418, as desired. For example, the implant 400 may include two, four, five, or more suture loops 418. It is contemplated that the suture loops 418 may be positioned at regular or even intervals throughout the overall length of the implant 400. However, in other embodiments, the suture loops 418 may be positioned at eccentric or uneven intervals along the length of the implant 400, as desired. It is contemplated that the suture loops 418 may be positioned to facilitate retrieval, repositioning, and/or reshaping of the stent 400. For example, in a stent 400 having two or more flared or enlarged regions, as in the AXIOS® stent made and distributed by Boston Scientific Corp., a first suture loop 418a may be positioned adjacent to the first flare and a second suture loop 418b may be positioned adjacent to the second flare.

In some embodiments, the implant 400 may include a first plurality of rings 424a, 424b, 424c (collectively, 424) adjacent the proximal end 404 of the implant, a second plurality of rings 426a, 426b, 426c (collectively, 426) adjacent the intermediate region 408 of the implant 400, and a third plurality of rings 428a, 428b, 428c (collectively, 428) adjacent the distal end 406 of the implant 400. The positioning of the rings 424, 426, 428 is not limited to the described and illustrated configuration. Rather, the positioning of the rings 424, 426, 428 may be determined by the desired location and quantity of the suture loops 418. For example, in some cases, a plurality of rings 424, 426, 428 may be positioned at each location where a suture loop 418 is desired. However, this is not required. In some instances, a suture loop 418 may be provided in the absence of a rings. Further, while each plurality of rings 424, 426, 428 is illustrated as including three rings, it is contemplate that each plurality of rings 424, 426, 428 may have fewer than three rings or more than three rings, as desired. Further, each plurality of rings 424, 426, 428 need not each have the same number of rings.

Each ring 424a, 424b, 424c of the first plurality of rings 424 may be positioned at a similar longitudinal distance (e.g., in a direction extending generally parallel to the longitudinal axis 430 of the implant 400). The rings 424 may be positioned about the circumference of the stent 400 at uniform intervals. For example, when three rings 424 are provided, the rings 424 may be separated by approximately 120°. However, the rings 424 may be eccentric or uneven intervals, as desired. In some cases, the rings 424 may not be positioned about an entire circumference of the stent frame 402. For example, if the suture loops 418 extend less an entire circumference or less than 360° about the stent 400, the rings 424 may be positioned to coincide with the portion of the circumference with which the suture loops 418 extend.

Each ring 426a, 426b, 426c of the second plurality of rings 426 may be positioned at a similar longitudinal distance (e.g., in a direction extending generally parallel to the longitudinal axis 430 of the implant 400). The rings 426 may be positioned about the circumference of the stent 400 at uniform intervals. For example, when three rings 426 are provided, the rings 426 may be separated by approximately 120°. However, the rings 426 may be eccentric or uneven intervals, as desired. In some cases, the rings 426 may not be positioned about an entire circumference of the stent frame 402. For example, if the suture loops 418 extend less an entire circumference or less than 360° about the stent 400, the rings 426 may be positioned to coincide with the portion of the circumference with which the suture loops 418 extend.

Each ring 428a, 428b, 428c of the third plurality of rings 428 may be positioned at a similar longitudinal distance (e.g., in a direction extending generally parallel to the longitudinal axis 430 of the implant 400). The rings 428 may be positioned about the circumference of the stent 400 at uniform intervals. For example, when three rings 428 are provided, the rings 428 may be separated by approximately 120°. However, the rings 428 may be at eccentric or uneven intervals, as desired. In some cases, the rings 428 may not be positioned about an entire circumference of the stent frame 402. For example, if the suture loops 418 extend less an entire circumference or less than 360° about the stent 400, the rings 428 may be positioned to coincide with the portion of the circumference with which the suture loops 418 extend.

In some embodiments, one, two or more, or all of the suture loops 418 may extend entirely around the circumference (e.g., 360°) of the stent frame 402. In other embodiments, one, two or more, or all of the suture loops 418 may extend less than 360° about the circumference of the stent frame 402. In some embodiments, one or more of the suture loops 418 may extend 350° or less, 300° or less, 270° or less, 225° or less, 180° or less, 135° or less, etc. In yet other embodiments, one, two or more, or all of the suture loops may extend more than 360° about the circumference of the stent frame 402.

As described above, the suture loops 418 may be formed from a retrieval suture 416. It is contemplated that the suture 416 may be threaded or passed through the openings of the rings 424, 426, 428 in place of or in addition to interweaving the suture 418 with the stent frame 402. It is contemplated that threading the suture 416 through the rings 424, 426, 428 instead of the stent frame 402 or by using the rings to at least partially reduce the length of suture 416 that is interwoven with the stent frame 402 reduces the force required to actuate the suture 416 by reducing the frictional forces exerted on the suture 416.

It is contemplated that when the suture 416 is only passed through the opening of the rings 424, 426, 428, the rings 424, 426, 428 may be fixedly attached to the stent frame 402. This may allow movement of the rings 424, 426, 428 to be translated to the stent frame 402. In some cases, the first plurality of rings 424 and the third plurality of rings 428 (e.g., the rings positioned adjacent to the proximal end 404 and the distal end 406) may be fixedly coupled to the stent frame 402 while the second plurality of rings 426 may be movably coupled to the stent frame 402. This is just one example. The rings 424, 426, 428 may be fixedly or movably coupled in any configuration desired. Further, some rings of each plurality may be fixedly coupled while others of the same plurality are movably coupled to the stent frame 402. It is contemplated that when the rings 424, 426, 428 are movably coupled to the stent frame 402, the suture 416 may be at least partially interwoven with the stent frame 402 near the movable rings 424, 426, 428 such that movement of the suture 416 is translated to the stent frame 402.

The suture 416 may have a first end 420 coupled to a first ring 424a in the first plurality of rings 424 and a second end 422 coupled to a first ring 428a in the third plurality of rings 428. The suture 416 be interwoven with the rings 424, 426, 428 and/or stent frame 402 in any number of ways. In one example, the first end 420 of the suture 416 may be coupled to the first ring 424a in the first plurality of rings 424. The second end 422 of the suture 416 may be threaded through the opening in the second ring 424b and then through the opening in the third ring 424c. The suture 416 may then be passed through the opening in the first ring 424a to form the first suture loop 418a. While the suture 416 is described as being threaded in a clockwise direction, the reverse configuration is also contemplated. As described above, the first plurality of rings 424 may be fixedly coupled to the stent frame 402 such that the suture 416 is not required to be interwoven with the stent frame 402 in order to manipulate the stent frame 402 adjacent to the first plurality of rings 424.

Once the suture 416 has passed through the opening in the first ring 424a, the suture 416 may be directed towards a first ring 426a in the second plurality of rings 426. In some cases, the second plurality of rings 426 may be circumferentially offset from the first plurality of rings 424. In such an instance, the longitudinally extending segment 432 of the suture 416 which extends between the first plurality of rings 424 and the second plurality of rings 426 may extend at a non-orthogonal angle to the plane formed by the second plurality of rings 426. In some cases, the longitudinally extending segment 432 may include rings in place of or in addition to the rings 424, 426, 428 at the suture loops 418.

The second end 422 of the suture 416 may be passed through the opening in the first ring 426a. The suture 416 may then be directed towards and through the opening in the third ring 426c (e.g., in a direction opposite the first suture loop 418a, although this is not required). The suture 416 may then be directed from the third ring 426c towards and through the second ring 426b. The suture 416 may then be passed through the opening in the first ring 426a to form the second suture loop 418b. When the second plurality of rings 426 is not fixedly coupled to the stent frame 402, the suture 416 may be at least partially interwoven with the stent frame between the first ring 426a and the third ring 426c, between the third ring 426c and the second ring 426b, and/or between the second ring 426b and the first ring 426a.

Once the suture 416 has passed through the opening in the first ring 426a to complete the suture loop 418b, the suture 416 may be directed towards a first ring 428a in the third plurality of rings 428. In some cases, the third plurality of rings 428 may be circumferentially offset from the second plurality of rings 426. In such an instance, the longitudinally extending segment 434 of the suture 416 which extends between the second plurality of rings 426 and the third plurality of rings 428 may extend at a non-orthogonal angle to the plane formed by the third plurality of rings 428. In some cases, the longitudinally extending segment 434 may include rings in place of or in addition to the rings 424, 426, 428 at the suture loops 418.

The second end 422 of the suture 416 may be passed through the opening in the first ring 428a. The suture 416 may then be directed towards and through the opening in the second ring 428b (e.g., in a direction opposite the second suture loop 418b, although this is not required). The suture 416 may then be directed from the second ring 428b towards and through the third ring 428c. The suture 416 may then be passed and coupled to the first ring 428a to form the third suture loop 418c. As described above, the third plurality of rings 428 may be fixedly coupled to the stent frame 402 such that the suture 416 is not required to be interwoven with the stent frame 402 in order to manipulate the stent frame 402 adjacent to the third plurality of rings 428.

To collapse, reposition, or reshape the implant 400, the suture 416 may be gripped at any location between the first end 420 and the second end 422 or at any of the rings 424, 426, 428 and pulled or otherwise actuated in a proximal direction. In some cases, the suture 416 may be provided with extra length or slack to allow the suture 416 to be gripped easier. In some cases, the extra length may be most apparent in the longitudinally extending segments 432, 434. In other embodiments, the suture 416 may be actuated in a distal direction. It is contemplated that the direction of actuation (e.g., proximal or distal) required to actuate the suture 416 may be dependent on the direction in which the suture 416 is interwoven with the stent frame 402. As suture 416 is actuated, the suture loops 418 begin to constrain or reduce the diameter (not explicitly shown) of the implant 400. The suture loop 418, 418b, 418c which constrains first may be dependent on where the suture 416 is gripped. For example, the suture loop 418 closest to the grip location may constrain first. Continued actuation of the suture 416 may cause the suture loops 418 further from the grip location to constrain or reduce in diameter.

Figure 11:
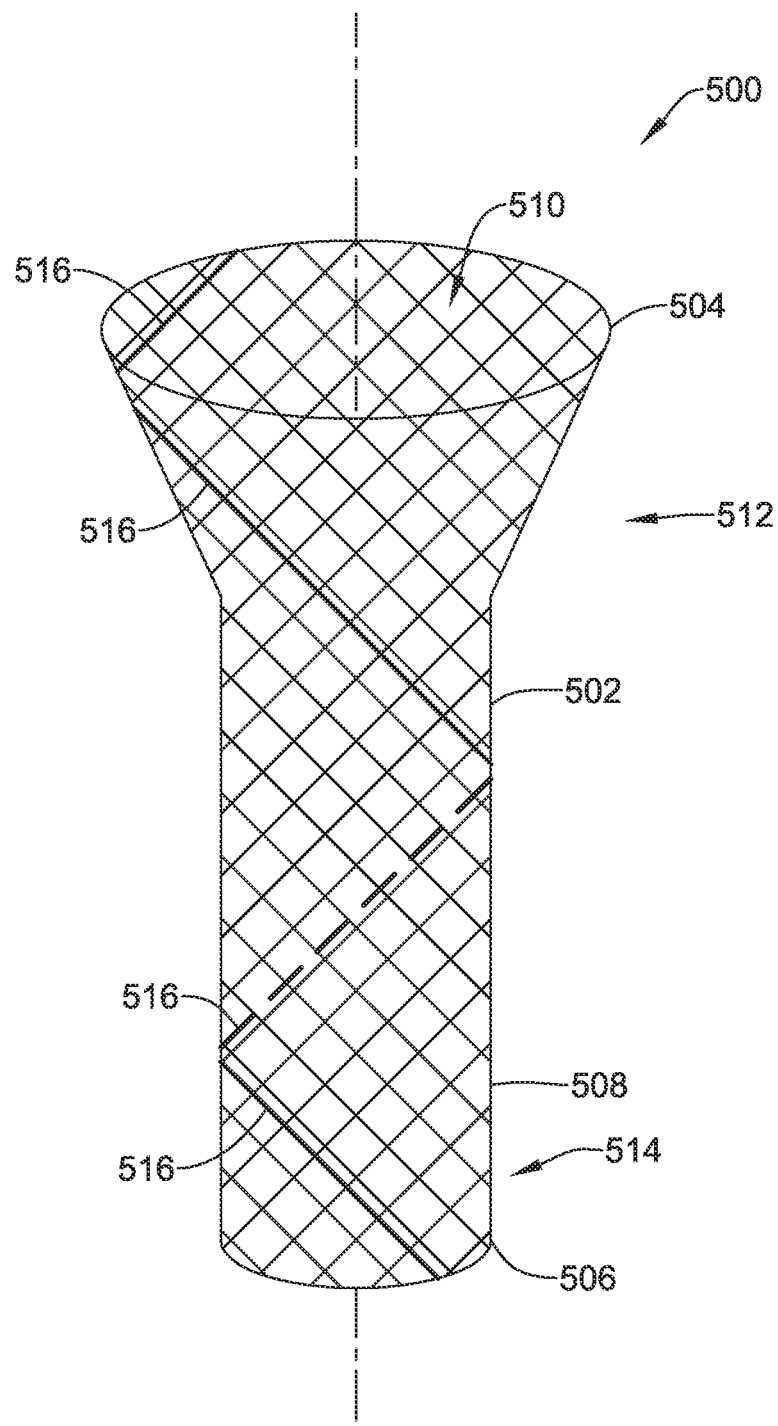
FIG. 11 is a side view of another illustrative implant with a retrieval suture in a first configuration.
Figure 12:
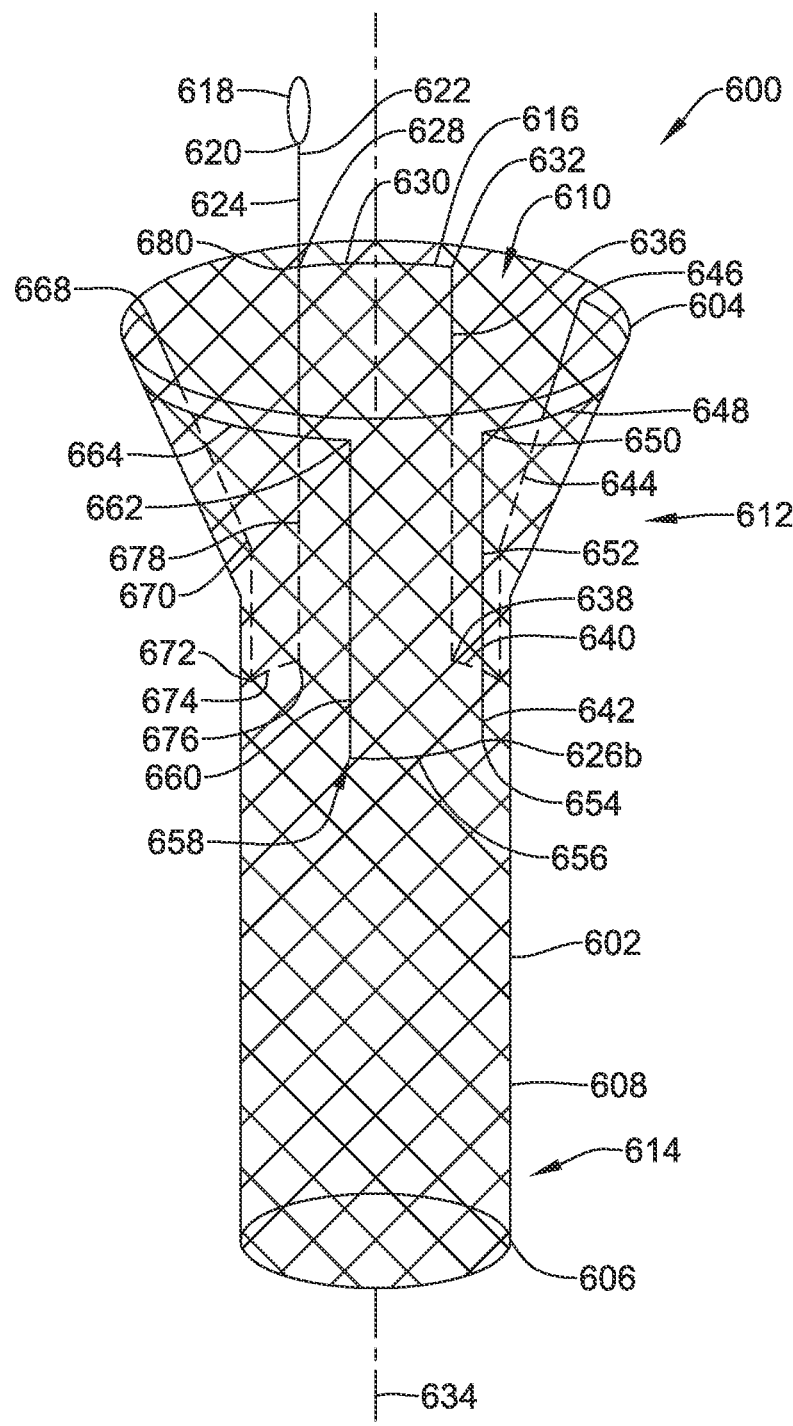
FIG. 12 is a side view of another illustrative implant with a retrieval suture in a first configuration.

FIG. 11 illustrates a side view of an illustrative endoluminal implant or stent 500. In some instances, the stent 500 may be formed from an elongated tubular stent frame 502. While the stent 500 is described as generally tubular, it is contemplated that the stent 500 may take any cross-sectional shape desired. The stent 500 may have a first, or proximal end 504, a second, or distal end 506, and an intermediate region 508 disposed between the first end 504 and the second end 506. The stent 500 may include a lumen 510 extending from a first opening adjacent the first end 504 to a second opening adjacent to the second end 506 to allow for the passage of food, fluids, etc.

The stent 500 may be expandable from a first radially collapsed configuration (not explicitly shown) to a second radially expanded configuration. In some cases, the stent 500 may be deployed to a configuration between the collapsed configuration and a fully expanded configuration. The stent 500 may be structured to extend across a stricture and to apply a radially outward pressure to the stricture in a lumen to open the lumen and allow for the passage of foods, fluids, air, etc.

The stent frame 502 may have a woven structure, fabricated from a number of filaments. In some embodiments, the stent frame 502 may be braided with one filament. In other embodiments, the stent frame 502 may be braided with several filaments, as is found, for example, in the WALL-FLEX®, WALLSTENT®, and POLYFLEX® stents, made and distributed by Boston Scientific Corp. In another embodiment, the stent frame 502 may be knitted, such as the ULTRAFLEX™ stents made by Boston Scientific Corp. In yet another embodiment, the stent frame 502 may be of a knotted type, such the PRECISION COLONIC™ stents made by Boston Scientific Corp. In still another embodiment, the stent frame 502 may be laser cut, such as the EPIC™ stents made by Boston Scientific Corp.

It is contemplated that the stent 500 can be made from a number of different materials such as, but not limited to, metals, metal alloys, shape memory alloys, and/or polymers, as desired, enabling the stent 500 to be expanded into shape when accurately positioned within the body. In some instances, the material may be selected to enable the stent 500 to be removed with relative ease as well. For example, the stent 500 can be formed from alloys such as, but not limited to, Nitinol and ELGILOY®. Depending on the material selected for construction, the stent 500 may be self-expanding (i.e., configured to automatically radially expand when unconstrained). In some embodiments, fibers may be used to make the stent 500, which may be composite fibers, for example, having an outer shell made of Nitinol having a platinum core. It is further contemplated the stent 500 may be formed from polymers including, but not limited to, polyethylene terephthalate (PET). In some embodiments, the stent 500 may be self-expanding while in other embodiments, the stent 500 may be expand by an expansion device (such as, but not limited to a balloon inserted within the lumen 510 of the stent 500). As used herein the term "self-expanding" refers to the tendency of the stent to return to a preprogrammed diameter when unrestrained from an external biasing force (for example, but not limited to a delivery catheter or sheath). The stent 500 may include a one-way valve, such as an elastomeric slit valve or duck bill valve, positioned within the lumen 510 thereof to prevent retrograde flow of gastrointestinal fluids.

In some instances, in the radially expanded configuration, the stent 500 may include a first end region 512 proximate the proximal end 504 and a second end region 514 proximate the second end 506. In some embodiments, the first end region 512 and the second end region 514 may include retention features or anti-migration flared regions (not explicitly shown at the second end region 514) having enlarged diameters relative to the intermediate portion 508. The anti-migration flared regions, which may be positioned adjacent to the first end 504 and the second end 506 of the stent 500, may be configured to engage an interior portion of the walls of the esophagus, stomach or other body lumen. In some embodiments, the retention features, or flared regions may have a larger diameter than the cylindrical intermediate region 508 of the stent 500 to prevent the stent 500 from migrating once placed in the esophagus, stomach, or other body lumen. It is contemplated that a transition from the cross-sectional area of the intermediate region 508 to the retention features or flared regions may be gradual, sloped, or occur in an abrupt step-wise manner, as desired. In other embodiments, the stent 500 may have a uniform diameter from the proximal end 504 to the distal end 506.

It is contemplated that the stent 500 can be made from a number of different materials such as, but not limited to, metals, metal alloys, shape memory alloys and/or polymers, as desired, enabling the stent 500 to be expanded into shape when accurately positioned within the body. In some instances, the material may be selected to enable the stent 500 to be removed with relative ease as well. For example, the stent 500 can be formed from alloys such as, but not limited to, Nitinol and ELGILOY®. Depending on the material selected for construction, the stent 500 may be self-expanding or require an external force to expand the stent 500. In some embodiments, composite filaments may be used to make the stent 500, which may include, for example, an outer shell or cladding made of Nitinol and a core formed of platinum or other radiopaque material. It is further contemplated the stent 500 may be formed from polymers including, but not limited to, polyethylene terephthalate (PET). In some instances, the filaments of the stent 500, or portions thereof, may be bioabsorbable or biodegradable, while in other instances the filaments of the stent 500, or portions thereof, may be biostable.

The implant 500 may be may be entirely, substantially or partially, covered with a polymeric covering, such as a coating (not explicitly shown). The covering may be disposed on an inner surface and/or outer surface of the implant 500, as desired. When so provided a polymeric covering may reduce or eliminate tissue ingrowth and/or reduce food impaction.

The implant 500 may further include a suture 516. The suture 516 may be formed as a part of the stent frame 502. For example, the suture 516 may be braided with, knitted with, or otherwise included in the stent frame 502 during the manufacture of the stent 500. In other words, one or more of the filaments of the stent frame 502 may be replaced with a suture 516. The suture 516 may be formed from a material having different mechanical properties from the remainder of the stent frame 502. For example, the suture 516 may be more elastic than the remainder of the stent frame 502. The suture 516 may be formed with the stent frame 502 such that it has some extra length or slack. This may allow the suture 516 to sag or protrude into the lumen 510 of the stent to allow the suture 516 to be more apparent to the physician.

To collapse, reposition, or reshape the implant 500, the suture 516 may be gripped at any location between the first end 504 and the second end 506 of the stent 500 and pulled or otherwise actuated in a proximal direction. In other embodiments, the suture 516 may be actuated in a distal direction. It is contemplated that the direction of actuation (e.g., proximal or distal) required to actuate the suture 516 may be dependent on the direction in which the suture 516 is wound or knitted with the stent frame 502. As suture 516 is actuated, the suture 516 may contract the stent frame 502 axially and circumferentially begin to constrain or reduce the diameter (not explicitly shown) of the implant 500. The portion of the stent frame 502 which constrains first may be dependent on where the suture 516 is gripped. For example, the stent frame 502 closest to the grip location may constrain first. Continued actuation of the suture 516 may cause the stent frame 502 further from the grip location to constrain or reduce in diameter.

FIG. 11 illustrates a side view of an illustrative endoluminal implant or stent 600. In some instances, the stent 600 may be formed from an elongated tubular stent frame 602. While the stent 600 is described as generally tubular, it is contemplated that the stent 600 may take any cross-sectional shape desired. The stent 600 may have a first, or proximal end 604, a second, or distal end 606, and an intermediate region 608 disposed between the first end 604 and the second end 606. The stent 600 may include a lumen 610 extending from a first opening adjacent the first end 604 to a second opening adjacent to the second end 606 to allow for the passage of food, fluids, etc.

The stent 600 may be expandable from a first radially collapsed configuration (not explicitly shown) to a second radially expanded configuration. In some cases, the stent 600 may be deployed to a configuration between the collapsed configuration and a fully expanded configuration. The stent 600 may be structured to extend across a stricture and to apply a radially outward pressure to the stricture in a lumen to open the lumen and allow for the passage of foods, fluids, air, etc.

The stent frame 602 may have a woven structure, fabricated from a number of filaments. In some embodiments, the stent frame 602 may be braided with one filament. In other embodiments, the stent frame 602 may be braided with several filaments, as is found, for example, in the WALLFLEX®, WALLSTENT®, and POLYFLEX® stents, made and distributed by Boston Scientific Corp. In another embodiment, the stent frame 602 may be knitted, such as the ULTRAFLEX™ stents made by Boston Scientific Corp. In yet another embodiment, the stent frame 602 may be of a knotted type, such the PRECISION COLONIC™ stents made by Boston Scientific Corp. In still another embodiment, the stent frame 602 may be laser cut, such as the EPIC™ stents made by Boston Scientific Corp.

It is contemplated that the stent 600 can be made from a number of different materials such as, but not limited to, metals, metal alloys, shape memory alloys and/or polymers, as desired, enabling the stent 600 to be expanded into shape when accurately positioned within the body. In some instances, the material may be selected to enable the stent 600 to be removed with relative ease as well. For example, the stent 600 can be formed from alloys such as, but not limited to, Nitinol and ELGILOY®. Depending on the material selected for construction, the stent 600 may be self-expanding (i.e., configured to automatically radially expand when unconstrained). In some embodiments, fibers may be used to make the stent 600, which may be composite fibers, for example, having an outer shell made of Nitinol having a platinum core. It is further contemplated the stent 600 may be formed from polymers including, but not limited to, polyethylene terephthalate (PET). In some embodiments, the stent 600 may be self-expanding while in other embodiments, the stent 600 may be expand by an expansion device (such as, but not limited to a balloon inserted within the lumen 610 of the stent 600). As used herein the term "self-expanding" refers to the tendency of the stent to return to a preprogrammed diameter when unrestrained from an external biasing force (for example, but not limited to a delivery catheter or sheath). The stent 600 may include a one-way valve, such as an elastomeric slit valve or duck bill valve, positioned within the lumen 610 thereof to prevent retrograde flow of gastrointestinal fluids.

In some instances, in the radially expanded configuration, the stent 600 may include a first end region 612 proximate the proximal end 604 and a second end region 614 proximate the second end 606. In some embodiments, the first end region 612 and the second end region 614 may include retention features or anti-migration flared regions (not explicitly shown at the second end region 614) having enlarged diameters relative to the intermediate portion 608. The anti-migration flared regions, which may be positioned adjacent to the first end 604 and the second end 606 of the stent 600, may be configured to engage an interior portion of the walls of the esophagus, stomach or other body lumen. In some embodiments, the retention features, or flared regions may have a larger diameter than the cylindrical intermediate region 608 of the stent 600 to prevent the stent 600 from migrating once placed in the esophagus, stomach, or other body lumen. It is contemplated that a transition from the cross-sectional area of the intermediate region 608 to the retention features or flared regions may be gradual, sloped, or occur in an abrupt step-wise manner, as desired. In other embodiments, the stent 600 may have a uniform diameter from the proximal end 604 to the distal end 606.

It is contemplated that the stent 600 can be made from a number of different materials such as, but not limited to, metals, metal alloys, shape memory alloys and/or polymers, as desired, enabling the stent 600 to be expanded into shape when accurately positioned within the body. In some instances, the material may be selected to enable the stent 600 to be removed with relative ease as well. For example, the stent 600 can be formed from alloys such as, but not limited to, Nitinol and ELGILOY®. Depending on the material selected for construction, the stent 600 may be self-expanding or require an external force to expand the stent 600. In some embodiments, composite filaments may be used to make the stent 600, which may include, for example, an outer shell or cladding made of Nitinol and a core formed of platinum or other radiopaque material. It is further contemplated the stent 600 may be formed from polymers including, but not limited to, polyethylene terephthalate (PET). In some instances, the filaments of the stent 600, or portions thereof, may be bioabsorbable or biodegradable, while in other instances the filaments of the stent 600, or portions thereof, may be biostable.

The implant 600 may be may be entirely, substantially or partially, covered with a polymeric covering, such as a coating (not explicitly shown). The covering may be disposed on an inner surface and/or outer surface of the implant 600, as desired. When so provided a polymeric covering may reduce or eliminate tissue ingrowth and/or reduce food impaction.

The implant 600 may further include a retrieval suture 616. The suture 616 may include a retrieval suture loop 618 which may be configured to be grasped by forceps or other tool during a clinical procedure for stent removal and or repositioning. In some cases, the retrieval suture loop 618 may be formed by tying a knot 620 between, or otherwise coupling (e.g., heat bonding, adhesive, etc.) a first end 622 and a second end 624 of the retrieval suture. In other embodiments, the retrieval suture loop 618 may be formed at either the first end 622 or the second end 624 of the retrieval suture 616. In such an instance, the end 622, 624 free from the retrieval suture loop 618 may be coupled to the stent 600 or the opposing end 622, 624 of the retrieval suture 616, although this is not required.

The suture 616 may be interwoven with the stent frame 602 at intervals along a length of the implant 600 to create a plurality of suture loops 626a, 626b (collectively, 626). While the illustrative implant 600 is shown and described has having two suture loops 626, it is contemplated that the implant 600 may include more than two suture loops 626, as desired. For example, the implant 600 may include three, four, five, or more suture loops 626. It is contemplated that the suture loops 626 may be positioned at regular or even intervals throughout the overall length of the implant 600. However, in other embodiments, the suture loops 626 may be positioned at eccentric or uneven intervals along the length of the implant 600, as desired. It is contemplated that the suture loops 626 may be positioned to facilitate retrieval, repositioning, and/or reshaping of the stent 600. For example, in a stent 600 having two or more flared or enlarged regions, as in the AXIOS® stent made and distributed by Boston Scientific Corp., a first retrieval suture loop 626a may be positioned adjacent to the first flare and a second retrieval suture loop 626b may be positioned adjacent to the second flare.

In some embodiments, one, two or more, or all of the suture loops 626 may extend entirely around the circumference (e.g., 360°) of the stent frame 602. In other embodiments, one, two or more, or all of the suture loops 626 may extend less than 360° about the circumference of the stent frame 602. In some embodiments, one or more of the suture loops 626 may extend 3634° or less, 300° or less, 270° or less, 225° or less, 180° or less, 135° or less, etc. In yet other embodiments, one, two or more, or all of the suture loops may extend more than 360° about the circumference of the stent frame 602. In the yet other embodiments, the suture loops 626 may be positioned such that individually the loops 626a, 626b extend less than the 360° about the circumference of the stent frame 602 but collectively extend about 360° about the circumference, as illustrated in FIG. 11.

The suture loops 626 may be formed from a single unitary suture 616. It is contemplated that the suture 616 may be interwoven with the stent frame 602 such that segments of the suture loops 626 may be constrained in a predetermined sequential order. In some cases, the proximal loop 626a and/or the distal loop 626b may not extend in a continuous loop. Rather, the proximal loop 626a and/or distal loop 626b may be broken into sections by longitudinally extending interconnecting segments 638, 644, 652, 660, 670, 678 which extend between the proximal loop 626a and the distal loop 626b.

The suture 616 may be interwoven with the stent frame 602 by threading one of the ends 622, 624 around the proximal end 604 of the implant 600 beginning at a first circumferential location 628 and moving (e.g., threading) in a first direction. In the illustrative example, the suture 616 is described as initially being threaded in a clockwise direction. However, the reverse configuration in which the suture is initially threaded in a counterclockwise direction is also contemplated. The suture 616 may be threaded around about one sixth (e.g., 60°) of the circumference of the implant 600 such that a first segment 630 of the suture 616 extends between the first circumferential location 628 and a second circumferential location 632. The first and second circumferential locations 628, 632 may be positioned at a similar longitudinal distance (e.g., in a direction extending generally parallel to the longitudinal axis 634 of the implant 600) from the first end 604 of the implant 600. In some cases, the suture 616 may be threaded such that it is interwoven with the stent frame 602 such that a portion of the suture 616 is within the lumen 610 of the implant 600 and a portion of the suture 616 is positioned along an exterior surface of the implant 600 (e.g., such that it will be in contact with a vessel lumen when the implant 600 is deployed within the body). At the second circumferential location 632, the suture 616 may be threaded along a length of implant 600 in a direction towards the second end 606 such that a second longitudinally extending interconnecting segment 638 of the suture 616 extends along a length of the implant 600 in a generally linear direction. The length of the second segment 638 of the suture 616 may vary depending on the application. For example, some implants 600 may include radially extending quills (not explicitly shown) configured to engage a body tissue. The second segment 638 may be configured to extend along a length equal to or greater to a length of the implant 600 including the radially extending quills. This is just one example. Other features of the implant 600, such as, but not limited to, the length of the implant 600 may be used to determine the length of the second segment 638 of the suture 616.

The second segment 638 of the suture 616 may extend from the second circumferential location 632 to a third circumferential location 638. The second circumferential location and the third circumferential location 638 may be at similar radial points about the circumference of the implant 600 but spaced a distance along the length thereof. At the third circumferential location 638, a third segment 640 of the suture 616 may be threaded radially about the circumference of the implant 600 in the first direction (e.g., clockwise). The third segment 640 may extend between the third circumferential location 638 and a fourth circumferential location 642 for about one sixth (e.g., 60°) of the circumference of the implant 600 to form a portion of the suture loop 626b.

At the fourth circumferential location 642, the suture 616 may be threaded along a length of implant 600 in a direction towards the first end 604 such that a fourth longitudinally extending interconnecting segment 644 of the suture 616 extends along a length of the implant 600 in a direction parallel to the longitudinal axis 634. The length of the fourth segment 644 of the suture 616 may be about the same length as the second segment 638 of the suture 616. The fourth segment 644 of the suture 616 may extend between the fourth circumferential location 642 and a fifth circumferential location 646. In some cases, the second and/or fourth segments 638, 644 of the suture may not be interwoven with the stent body 602 but rather extend along an inner or outer surface of the stent frame 602. In some embodiments, the first, second, and fifth circumferential locations 628, 632, 646 may be positioned at a similar longitudinal distance (e.g., in a direction extending generally parallel to the longitudinal axis 634 of the implant 600) from the first end 604 of the implant 600.

From the fifth circumferential location 646, the suture 616 may be threaded through the stent body 602 in the first direction (e.g., away from the first segment 630) to form a fifth segment 648 of the suture 616. The fifth segment 648 of the suture 616 may be threaded through the stent frame 602 to a sixth circumferential location 650. The suture 616 may be threaded around about one sixth (e.g., 60°) of the circumference of the implant 600 to form a portion of the proximal loop 626a.

At the sixth circumferential location 650, the suture 616 may be threaded along a length of implant 600 in a direction towards the second end 606 such that a sixth longitudinally extending interconnecting segment 652 of the suture 616 extends along a length of the implant 600 in a generally linear direction. The length of the sixth segment 652 of the suture 616 may be about the same length as the second segment 654 and/or fourth segment 644 of the suture 616.

The sixth segment 652 of the suture 616 may extend from the sixth circumferential location 650 to a seventh circumferential location 654. The sixth circumferential location 650 and the seventh circumferential location 654 may be at similar radial points about the circumference of the implant 600 but spaced a distance along the length thereof. At the seventh circumferential location 654, a seventh segment 656 of the suture 616 may be threaded radially about the circumference of the implant 600 in the first direction (e.g., clockwise). The seventh segment 656 may extend between the seventh circumferential location 654 and an eighth circumferential location 658 for about one sixth (e.g., 60°) of the circumference of the implant 600 to form a portion of the suture loop 626b. At the eighth circumferential location 658, the suture 616 may be threaded along a length of implant 600 in a direction towards the first end 604 such that an eighth longitudinally extending interconnecting segment 660 of the suture 616 extends along a length of the implant 600 in a direction parallel to the longitudinal axis 634. The length of the eighth segment 660 of the suture 616 may be about the same length as the second, fourth, and sixth segments 636, 644, 652 of the suture 616. The eighth segment 660 of the suture 616 may extend between the eighth circumferential location 658 and a ninth circumferential location 662.

From the ninth circumferential location 662, the suture 616 may be threaded through the stent body 602 in the first direction (e.g., away from the fifth segment 648) to form a ninth segment 664 of the suture 616. The ninth segment 664 of the suture 616 may be threaded through the stent frame 602 to a tenth circumferential location 668. The suture 616 may be threaded around about one sixth (e.g., 60°) of the circumference of the implant 600 to form a portion of the proximal loop 626a.

At the tenth circumferential location 668, the suture 616 may be threaded along a length of implant 600 in a direction towards the second end 606 such that a tenth longitudinally extending interconnecting segment 670 of the suture 616 extends along a length of the implant 600 in a generally linear direction. The length of the tenth segment 670 of the suture 616 may be about the same length as the second, fourth, sixth, and eighth segments 654, 644, 652, 660 of the suture 616.

The tenth segment 670 of the suture 616 may extend from the tenth circumferential location 668 to an eleventh circumferential location 672. The tenth circumferential location 668 and the eleventh circumferential location 672 may be at similar radial points about the circumference of the implant 600 but spaced a distance along the length thereof. At the eleventh circumferential location 672, an eleventh segment 674 of the suture 616 may be threaded radially about the circumference of the implant 600 in the first direction (e.g., clockwise). The eleventh segment 674 may extend between the eleventh circumferential location 672 and a twelfth circumferential location 676 for about one sixth (e.g., 60°) of the circumference of the implant 600 to form a portion of the suture loop 626b.

At the twelfth circumferential location 676, the suture 616 may be threaded along a length of implant 600 in a direction towards the first end 604 such that a twelfth longitudinally extending interconnecting segment 678 of the suture 616 extends along a length of the implant 600 in a direction parallel to the longitudinal axis 634. The length of the twelfth segment 678 of the suture 616 may be about the same length as the second, fourth, sixth, eighth, and tenth segments 636, 644, 652, 660, 670 of the suture 616. The twelfth segment 678 of the suture 616 may extend between the twelfth circumferential location 676 and a thirteenth circumferential location 680. The thirteenth circumferential location 680 may be at approximately the same radial location as the first circumferential location 628. However, this is not required. For example, the first circumferential location 628 may be radially spaced from the thirteenth circumferential location 680 by, for example, 1° or less, 5° or less, 10° or less, 20° or less, etc. The first and second ends 620, 622 of the suture 616 may then be tied or secured as described above.

The proximal suture loop 626a may be formed from circumferentially discontinuous segments of the suture including the first segment 630, the fifth segment 648, and the ninth segment 664. The circumferential points forming each of these segments (e.g., first, second, fifth, sixth, ninth, and tenth circumferential points 628, 632, 646, 650, 662, 668) may be positioned at a similar longitudinal distance (e.g., in a direction extending generally parallel to the longitudinal axis 634 of the implant 600) from the first end 604 of the implant 600. The distal suture loop 626b may be formed from circumferentially discontinuous segments of the suture including the third segment 640, the seventh segment 656, and the eleventh segment 674. The circumferential points forming each of these segments (e.g., third, fourth, seventh, eighth, eleventh, and twelfth circumferential points 638, 642, 654, 658, 672, 676) may be positioned at a similar longitudinal distance (e.g., in a direction extending generally parallel to the longitudinal axis 634 of the implant 600) from the first end 604 of the implant 600.

While each of the circumferentially extending segments 630, 640, 648, 656, 664, 674 are described as extending approximately 60° about the circumference of the stent frame 602, this is not required. If it is desired for each circumferentially extending segment to be approximately uniform, the arc length of the circumferentially extending segment may be dependent on the number of circumferentially extending segments. It is further contemplated that the circumferentially extending segments need not all have the same arc length.

To collapse the implant 600, the retrieval suture loop 618, or a portion of the first suture loop 626a in the absence of the retrieval suture loop 618, may be pulled or otherwise actuated in a proximal direction. It is contemplated that the direction of actuation (e.g., proximal or distal) required to actuate the suture 616 may be dependent on the direction in which the suture 616 is interwoven with the stent frame 602. As the retrieval suture loop 618, or the first suture loop 626a in the absence of the retrieval suture loop 618, is actuated, the suture loops 626 begin to constrain or reduce the diameter of the implant 600. The orientation of the suture loops 626 may cause the suture loops 626 to constrain at substantially the same time. However, opposing sides of the proximal suture loop 626a and the distal suture loop 626b may constrain first.

The materials that can be used for the various components of the implants 10, 100, 200, (and variations, systems or components thereof disclosed herein) and the various elements thereof disclosed herein may include those commonly associated with medical devices. For simplicity purposes, the following discussion makes reference to the implants 10, 100, 200 (and variations, systems or components disclosed herein). However, this is not intended to limit the devices and methods described herein, as the discussion may be applied to other elements, members, components, or devices disclosed herein.

The implants 10, 100, 200 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of implants 10, 100, 200 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of implants 10, 100, 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of implants 10, 100, 200 to achieve the same result.

In some embodiments, a degree of Magnetic Resonance Imaging (MM) compatibility is imparted into implants 10, 100, 200. For example, implants 10, 100, 200 or portions thereof, may be made of a material that does not substantially distort the image and create substantial artifacts (i.e., gaps in the image). Certain ferromagnetic materials, for example, may not be suitable because they may create artifacts in an MM image. The implants 10, 100, 200 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for implants 10, 100, 200 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will appreciate that the different embodiments of the implant described here, their mode of operation, etc., are merely representative of the environment in which the present disclosure operates. Accordingly, a variety of alternatively shaped collaborating components may also be used as a substitutive for the purpose of engaging, steering and locating the stent at a desired target site, thus, not limiting the scope of the present disclosure. Further, the disclosed implants may be adequately stretchable, extendable, and retractable, allowing for its flexible deployment. More particularly, the configurations described here may be applicable for other medical applications as well, and accordingly, a variety of other medical devices may be used in combination with the implant. Those medical devices may include biopsy forceps, scissors, lithotripters, dilators, other cautery tools, and the like.

Further, while the implant is generally described along with an exemplary rigid and flexible region(s), a variety of other configurations and arrangements may also be contemplated and conceived as well. In addition, the operations, devices, and components, described herein may be equally applicable for other purposes where a component is required to be positioned in places where a leakage needs to be avoided or other treatments are desired. Embodiments of the present disclosure are thus applicable to medical and/or non-medical environments. Further, certain aspects of the aforementioned embodiments may be selectively used in collaboration, or removed, during practice, without departing from the scope of the disclosed embodiments.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. An implant comprising:
   a stent having a proximal end region, a distal end region, and a circumference; and
   a retrieval suture interwoven with the stent, the retrieval suture including:
      a first suture loop extending circumferentially around the stent and adjacent to a suture retrieval loop, and
      a second suture loop extending circumferentially around the stent and longitudinally spaced from the first suture loop;
   wherein the first suture loop and the second suture loop are coupled together via one or more longitudinal segments of the retrieval suture;
   wherein the first suture loop has an arc length of 225° or less of the circumference of the stent;
   wherein the second suture loop has an arc length of 225° or less of the circumference of the stent;
   wherein the first suture loop is a discontinuous loop comprising two or more circumferential segments of the retrieval suture.

2. The implant of claim 1, wherein at least one of the first and second suture loops has an arc length of 180° or less of the circumference of the stent.

3. The implant of claim 1, wherein at least 25% of the circumference of the stent is devoid of the retrieval suture disposed therein.

4. The implant of claim 1, wherein at least 50% of the circumference of the stent is devoid of the retrieval suture disposed therein.

5. The implant of claim 1, wherein the stent includes a plurality of barbs extending radially outward from one side of the stent.

6. The implant of claim 5, wherein the first suture loop extends circumferentially around the one side of the stent.

7. The implant of claim 6, wherein an opposite side of the stent from the one side of the stent is devoid of the first suture loop.

8. The implant of claim 5, wherein the second suture loop extends circumferentially around the one side of the stent.

9. The implant of claim 8, wherein an opposite side of the stent from the one side of the stent is devoid of the second suture loop.

10. The implant of claim 1, wherein the first suture loop is positioned adjacent to the proximal end region and the second suture loop is positioned adjacent to the distal end region.

11. The implant of claim 1, wherein a proximal force exerted on the suture retrieval loop is configured to partially collapse the stent radially inward.

12. The implant of claim 11, wherein the proximal force exerted on the suture retrieval loop is configured to partially collapse the stent radially inward to a greater extent along one side of the stent.

13. An implant comprising:
    a stent having a proximal end, a distal end, and a circumference; and
    a retrieval suture interwoven with the stent, the retrieval suture comprising:
       a first segment extending circumferentially between a first circumferential location and a second circumferential location;
       a second segment extending longitudinally between the second circumferential location and a third circumferential location;
       a third segment extending circumferentially between the third circumferential location and a fourth circumferential location and interwoven with the stent;
       a fourth segment extending longitudinally between the fourth circumferential location and a fifth circumferential location; and
       a fifth segment extending circumferentially between the fifth circumferential location and a sixth circumferential location;
    wherein the first, second, fifth, and sixth circumferential locations are at a first longitudinal distance from the proximal end of the stent and the third and fourth circumferential locations are at a second longitudinal distance, different from the first longitudinal distance, from the proximal end of the stent; and
    wherein the first and fifth segments together form a discontinuous first suture loop and the third segment forms a second suture loop; and
    wherein the first suture loop has an arc length of 180° or less of the circumference of the stent;
    wherein the second suture loop has an arc length of 180° or less of the circumference of the stent.

14. The implant of claim 13, wherein at least 50% of the circumference of the stent is devoid of the retrieval suture disposed therein.

15. The implant of claim 13, wherein the stent includes a plurality of barbs extending radially outward from a portion of the circumference of the stent having an arc length of 180° or less of the circumference of the stent.

16. The implant of claim 15, wherein the first suture loop and the second suture loop each extend circumferentially around the portion of the circumference of the stent including the plurality of barbs.

17. The implant of claim 16, wherein the first suture loop and the second suture loop each extend circumferentially only around the portion of the circumference of the stent including the plurality of barbs such that a remainder of the circumference of the stent is devoid of the first suture loop and the second suture loop.

18. The implant of claim 13, wherein the retrieval suture is a single unitary structure.

19. An implant comprising:
    a stent having a proximal end region, a distal end region, and a circumference; and
    a retrieval suture interwoven with the stent, the retrieval suture including:
       a first suture loop extending circumferentially around the stent and adjacent to a suture retrieval loop, and
       a second suture loop extending circumferentially around the stent and longitudinally spaced from the first suture loop;
    wherein the first suture loop and the second suture loop are coupled together via one or more longitudinal segments of the retrieval suture;
    wherein the stent includes a plurality of barbs extending radially outward from a portion of the circumference of the stent having an arc length of 180° or less of the circumference of the stent;
    wherein the first suture loop extends along the portion of the circumference of the stent including the plurality of barbs;
    wherein the second suture loop extends along the portion of the circumference of the stent including the plurality of barbs;
    wherein a proximal force exerted on the suture retrieval loop is configured to partially collapse the stent radially inward.

20. The implant of claim 19, wherein the proximal force exerted on the suture retrieval loop is configured to partially collapse the stent radially inward to a greater extent along the portion of the circumference of the stent including the plurality of barbs.

* * * * *